United States Patent
Shemer et al.

(10) Patent No.: US 9,713,723 B2
(45) Date of Patent: Jul. 25, 2017

(54) SIGNAL DELIVERY THROUGH THE RIGHT VENTRICULAR SEPTUM

(75) Inventors: Itzhak Shemer, Haifa (IL); Yuval Mika, Closter, NJ (US); Benny Rousso, Rishon-LeZion (IL)

(73) Assignee: Impulse Dynamics NV, Curacao (AN)

( * ) Notice: Subject to any disclaimer, the term of this patent is extended or adjusted under 35 U.S.C. 154(b) by 1223 days.

(21) Appl. No.: 11/673,812

(22) Filed: Feb. 12, 2007

(65) Prior Publication Data

US 2007/0162079 A1    Jul. 12, 2007

Related U.S. Application Data

(63) Continuation-in-part of application No. 10/672,385, filed on Sep. 26, 2003, now Pat. No. 7,187,970, which is a continuation of application No. 09/848,535, filed on May 3, 2001, now abandoned, said application No. 10/672,385 is a continuation-in-part of application No. 10/188,726, filed on Jul. 2, 2002, now Pat. No. 7,218,963, which is a continuation of application No. 09/254,903, filed as application No. PCT/IL97/00233 on Jul. 9, 1997, now Pat. No. 6,415,178, said
(Continued)

(30) Foreign Application Priority Data

Sep. 17, 1996    (IL) .......................................... 119261

(51) Int. Cl.
| | |
|---|---|
| *A61N 1/362* | (2006.01) |
| *A61N 1/368* | (2006.01) |
| *A61N 1/32* | (2006.01) |
| *A61N 1/365* | (2006.01) |

(52) U.S. Cl.
CPC ............ *A61N 1/3627* (2013.01); *A61N 1/368* (2013.01); *A61N 1/36585* (2013.01); *A61N 1/32* (2013.01); *A61N 1/36542* (2013.01); *A61N 1/36557* (2013.01); *A61N 1/36564* (2013.01)

(58) Field of Classification Search
CPC ..... A61N 1/368; A61N 1/3627; A61N 1/3684
USPC ...................................... 607/2, 9, 18, 25, 27
See application file for complete search history.

(56) References Cited

U.S. PATENT DOCUMENTS

| | | |
|---|---|---|
| 1,918,386 A | 7/1933 | Esau |
| 3,211,154 A | 10/1965 | Becker et al. |

(Continued)

FOREIGN PATENT DOCUMENTS

| | | |
|---|---|---|
| EP | 148 687 | 7/1985 |
| EP | 0148687 | 7/1985 |

(Continued)

OTHER PUBLICATIONS

Hoffman, B.F. et al., "Effects of Postextrasystolic Potentiation on Normal and Failing Hearts", Buttetin of New York Academy of Medicine, 41 in 1965, pp. 498-534.
(Continued)

*Primary Examiner* — Michael D Abreu

(57) ABSTRACT

A method is provided for use with a human subject. The method includes accessing a cardiac site via a vena cava of the subject, and alleviating heart failure of the subject by applying to the cardiac site, during a refractory period of the site, a refractory-period signal that affects the left ventricle of the subject's heart. Other embodiments are also described.

50 Claims, 7 Drawing Sheets

Related U.S. Application Data application No. 10/672,385 is a continuation-in-part of application No. 10/039,845, filed on Oct. 23, 2001, now Pat. No. 9,289,618, which is a continuation of application No. 09/563,544, filed on May 1, 2000, now Pat. No. 6,363,279, which is a continuation of application No. 09/101,723, filed as application No. PCT/IL97/00012 on Jan. 8, 1997, now Pat. No. 6,317,631.

(60) Provisional application No. 60/202,382, filed on May 4, 2000, provisional application No. 60/009,769, filed on Jan. 11, 1996, provisional application No. 60/011,117, filed on Feb. 5, 1996, provisional application No. 60/026,392, filed on Sep. 16, 1996.

(56) References Cited

U.S. PATENT DOCUMENTS

| | | |
|---|---|---|
| 3,541,390 A | 11/1970 | Jahnke |
| 3,572,345 A | 3/1971 | Auphan |
| 3,587,567 A | 6/1971 | Schiff |
| 3,651,805 A | 3/1972 | Breiling |
| 3,651,806 A | 3/1972 | Hirshberg |
| 3,796,221 A | 3/1974 | Hagfors |
| 3,911,930 A | 10/1975 | Hagfors et al. |
| 3,933,147 A | 1/1976 | Du Vall et al. |
| 3,942,536 A | 3/1976 | Mirowski et al. |
| 3,944,740 A | 3/1976 | Murase et al. |
| 3,952,750 A | 4/1976 | Mirowski et al. |
| 4,030,509 A | 6/1977 | Heilman et al. |
| 4,106,494 A | 8/1978 | McEachern |
| 4,164,216 A | 8/1979 | Person |
| 4,168,711 A | 9/1979 | Cannon, III et al. |
| 4,184,493 A | 1/1980 | Langer et al. |
| 4,202,340 A | 5/1980 | Langer et al. |
| 4,223,678 A | 9/1980 | Langer et al. |
| 4,237,895 A | 12/1980 | Johnson |
| 4,273,114 A | 6/1981 | Barkalow et al. |
| 4,293,734 A | 10/1981 | Pepper, Jr. |
| 4,312,354 A | 1/1982 | Walters |
| 4,315,503 A | 2/1982 | Ryaby et al. |
| 4,316,472 A | 2/1982 | Mirowski et al. |
| 4,337,776 A | 7/1982 | Daly et al. |
| 4,369,791 A | 1/1983 | Friedman |
| 4,384,585 A | 5/1983 | Zipes |
| 4,387,717 A | 6/1983 | Brownlee et al. |
| 4,403,614 A | 9/1983 | Engle et al. |
| 4,406,288 A | 9/1983 | Horwinski et al. |
| 4,407,288 A | 10/1983 | Langer et al. |
| 4,411,268 A | 10/1983 | Cox |
| 4,428,366 A | 1/1984 | Findl et al. |
| 4,440,172 A | 4/1984 | Langer |
| 4,506,680 A | 3/1985 | Stokes |
| 4,537,195 A | 8/1985 | McDonnell |
| 4,537,203 A | 8/1985 | Machida |
| 4,543,738 A | 10/1985 | Mower |
| 4,543,956 A * | 10/1985 | Herscovici ............ 607/13 |
| 4,550,221 A | 10/1985 | Mabusth |
| 4,554,922 A | 11/1985 | Prystowsky et al. |
| 4,554,992 A | 11/1985 | Kassai |
| 4,559,946 A | 12/1985 | Mower |
| 4,559,947 A | 12/1985 | Renger et al. |
| 4,566,456 A | 1/1986 | Koning et al. |
| 4,572,191 A | 2/1986 | Mirowski et al. |
| 4,628,934 A | 12/1986 | Pohndorf et al. |
| 4,637,397 A | 1/1987 | Jones et al. |
| 4,639,720 A | 1/1987 | Rympalski et al. |
| 4,651,716 A | 3/1987 | Forester et al. |
| 4,674,508 A | 6/1987 | DeCote |
| 4,679,572 A | 7/1987 | Baker, Jr. |
| 4,686,332 A | 8/1987 | Greanias et al. |
| 4,690,155 A | 9/1987 | Hess |
| 4,693,253 A | 9/1987 | Adams |
| 4,708,145 A | 11/1987 | Tacker et al. |
| 4,717,581 A | 1/1988 | Robblee |
| 4,726,279 A | 2/1988 | Kepler et al. |
| 4,726,379 A | 2/1988 | Altman et al. |
| 4,765,341 A | 8/1988 | Mower et al. |
| 4,807,632 A * | 2/1989 | Liess et al. ............ 600/333 |
| 4,830,006 A | 5/1989 | Haluska et al. |
| 4,834,100 A | 5/1989 | Charms |
| 4,850,959 A | 7/1989 | Findl |
| 4,870,974 A | 10/1989 | Wang |
| 4,878,553 A | 11/1989 | Yamanami et al. |
| 4,884,576 A | 12/1989 | Alt |
| 4,914,624 A | 4/1990 | Dunthorn et al. |
| 4,928,688 A | 5/1990 | Mower |
| 4,967,749 A | 11/1990 | Cohen |
| 4,971,058 A | 11/1990 | Pless et al. |
| 4,979,507 A | 12/1990 | Heinz et al. |
| 4,988,837 A | 1/1991 | Murakami et al. |
| 4,996,984 A | 3/1991 | Sweeney |
| 4,998,531 A | 3/1991 | Bocchi et al. |
| 4,998,532 A | 3/1991 | Griffith |
| 5,002,052 A | 3/1991 | Haluska et al. |
| 5,003,976 A | 4/1991 | Alt |
| 5,018,522 A | 5/1991 | Mehra |
| 5,020,544 A | 6/1991 | Dahl et al. |
| 5,022,396 A | 6/1991 | Watanabe |
| 5,026,397 A | 6/1991 | Aoki et al. |
| 5,031,617 A | 7/1991 | Klettner |
| 5,041,107 A | 8/1991 | Heil, Jr. |
| 5,044,375 A | 9/1991 | Bach, Jr. et al. |
| 5,048,522 A | 9/1991 | Petrofsky |
| 5,063,929 A | 11/1991 | Bartlet et al. |
| 5,067,940 A | 11/1991 | Liboff et al. |
| 5,083,564 A | 1/1992 | Scherlag |
| 5,085,218 A | 2/1992 | Heil et al. |
| 5,087,243 A | 2/1992 | Avitall |
| 5,097,832 A | 3/1992 | Buchanan |
| 5,097,833 A | 3/1992 | Campos |
| 5,097,843 A | 3/1992 | Soukup et al. |
| 5,101,814 A | 4/1992 | Palti |
| 5,107,834 A | 4/1992 | Ideker et al. |
| 5,111,814 A | 5/1992 | Goldfarb |
| 5,111,815 A | 5/1992 | Mower |
| 5,129,394 A | 7/1992 | Mehra |
| 5,133,354 A | 7/1992 | Kallok |
| 5,137,021 A | 8/1992 | Wayne et al. |
| 5,144,554 A | 9/1992 | Zhang et al. |
| 5,154,501 A | 10/1992 | Svenson et al. |
| 5,156,147 A | 10/1992 | Warren et al. |
| 5,156,149 A | 10/1992 | Hudrlik |
| 5,161,527 A | 11/1992 | Nappholz et al. |
| 5,163,427 A | 11/1992 | Keimel |
| 5,163,428 A | 11/1992 | Pless |
| 5,172,690 A | 12/1992 | Nappholz et al. |
| 5,172,699 A | 12/1992 | Svenson et al. |
| 5,174,286 A | 12/1992 | Chirife |
| 5,184,616 A | 2/1993 | Weiss |
| 5,184,620 A | 2/1993 | Cudahy et al. |
| 5,185,620 A | 2/1993 | Cooper |
| 5,188,104 A | 2/1993 | Wernicke et al. |
| 5,188,106 A | 2/1993 | Nappholz et al. |
| 5,190,041 A | 3/1993 | Palti |
| 5,199,428 A | 4/1993 | Obel et al. |
| 5,205,284 A | 4/1993 | Freeman |
| 5,213,098 A | 5/1993 | Bennett et al. |
| 5,231,381 A | 7/1993 | Duwaer |
| 5,233,985 A | 8/1993 | Hudrlik |
| 5,236,413 A | 8/1993 | Feiring |
| 5,243,980 A | 9/1993 | Mehra et al. |
| 5,267,560 A * | 12/1993 | Cohen ............ 607/25 |
| 5,281,219 A | 1/1994 | Kallok |
| 5,282,785 A | 2/1994 | Shapland et al. |
| 5,284,491 A | 2/1994 | Sutton et al. |
| 5,286,254 A | 2/1994 | Shapland et al. |
| 5,292,344 A | 3/1994 | Douglas |
| 5,305,745 A | 4/1994 | Zacouto |
| 5,318,591 A | 6/1994 | Causey et al. |
| 5,320,543 A | 6/1994 | Barton et al. |
| 5,320,642 A | 6/1994 | Scherlag |
| 5,320,643 A | 6/1994 | Roline et al. |

(56) References Cited

U.S. PATENT DOCUMENTS

| | | |
|---|---|---|
| 5,324,327 A | 6/1994 | Cohen |
| 5,325,856 A | 7/1994 | Nitzsche et al. |
| 5,327,887 A | 7/1994 | Nowakowski |
| 5,336,485 A | 8/1994 | Fariss |
| 5,346,506 A | 9/1994 | Mower et al. |
| 5,350,403 A | 9/1994 | Stroetmann et al. |
| 5,353,800 A | 10/1994 | Pohndorf et al. |
| 5,365,461 A | 11/1994 | Stein et al. |
| 5,366,486 A | 11/1994 | Zipes et al. |
| 5,368,040 A | 11/1994 | Carney |
| 5,370,665 A | 12/1994 | Hudrlik |
| 5,374,787 A | 12/1994 | Miller et al. |
| 5,381,160 A | 1/1995 | Landmeier |
| 5,386,835 A | 2/1995 | Elphick et al. |
| 5,386,837 A | 2/1995 | Sterzer |
| 5,387,419 A | 2/1995 | Levy et al. |
| 5,391,192 A | 2/1995 | Lu et al. |
| 5,391,199 A | 2/1995 | Ben-Haim |
| 5,397,344 A | 3/1995 | Garfield et al. |
| 5,398,683 A | 3/1995 | Edwards et al. |
| 5,402,151 A | 3/1995 | Duwaer |
| 5,405,365 A | 4/1995 | Hoegnelid et al. |
| 5,411,531 A * | 5/1995 | Hill et al. ............... 607/14 |
| 5,415,629 A | 5/1995 | Henley |
| 5,417,717 A | 5/1995 | Salo et al. |
| 5,419,763 A | 5/1995 | Hildebrand |
| 5,423,872 A | 6/1995 | Cigaina |
| 5,425,363 A | 6/1995 | Wang |
| 5,431,682 A | 7/1995 | Hedberg |
| 5,431,688 A | 7/1995 | Freeman |
| 5,431,693 A | 7/1995 | Schroeppel |
| 5,433,730 A | 7/1995 | Alt |
| 5,443,485 A | 8/1995 | Housworth et al. |
| 5,443,489 A | 8/1995 | Ben-Haim |
| 5,445,609 A | 8/1995 | Lattin et al. |
| 5,447,520 A | 9/1995 | Spano et al. |
| 5,447,525 A | 9/1995 | Powell et al. |
| 5,447,526 A | 9/1995 | Karsdon |
| 5,458,568 A | 10/1995 | Racchini et al. |
| 5,464,020 A | 11/1995 | Lerner |
| 5,464,429 A | 11/1995 | Hedberg et al. |
| 5,468,254 A | 11/1995 | Hahn et al. |
| 5,472,453 A | 12/1995 | Alt |
| 5,476,484 A | 12/1995 | Hedberg |
| 5,476,485 A | 12/1995 | Weinberg et al. |
| 5,476,487 A * | 12/1995 | Sholder ............... 607/28 |
| 5,476,497 A | 12/1995 | Mower et al. |
| 5,480,422 A | 1/1996 | Ben-Haim |
| 5,482,052 A | 1/1996 | Lerner |
| 5,489,293 A | 2/1996 | Pless et al. |
| 5,495,077 A | 2/1996 | Miller et al. |
| 5,499,971 A | 3/1996 | Shapland et al. |
| 5,501,662 A | 3/1996 | Hofmann |
| 5,505,700 A | 4/1996 | Leone et al. |
| 5,510,813 A | 4/1996 | Makinwa et al. |
| 5,514,162 A | 5/1996 | Bornzin et al. |
| 5,520,642 A | 5/1996 | Bigagli et al. |
| 5,522,853 A | 6/1996 | Kroll |
| 5,527,345 A | 6/1996 | Infinger |
| 5,528,002 A | 6/1996 | Katabami |
| 5,531,764 A | 7/1996 | Adams et al. |
| 5,534,015 A | 7/1996 | Kroll et al. |
| 5,540,722 A | 7/1996 | Clare et al. |
| 5,540,730 A | 7/1996 | Terry, Jr. et al. |
| 5,540,734 A | 7/1996 | Zabara |
| 5,543,589 A | 8/1996 | Buchana et al. |
| 5,546,951 A | 8/1996 | Ben-Haim |
| 5,549,646 A | 8/1996 | Katz et al. |
| 5,556,421 A | 9/1996 | Prutchi et al. |
| 5,556,760 A | 9/1996 | Nakamura et al. |
| 5,558,640 A | 9/1996 | Pfeiler et al. |
| 5,561,165 A | 10/1996 | Lautt et al. |
| 5,562,708 A | 10/1996 | Combs et al. |
| 5,565,632 A | 10/1996 | Ogawa |
| 5,568,809 A | 10/1996 | Ben-haim |
| 5,571,143 A | 11/1996 | Hoegnelid et al. |
| 5,571,997 A | 11/1996 | Gray et al. |
| 5,578,061 A | 11/1996 | Stroetmann et al. |
| 5,584,803 A | 12/1996 | Stevens et al. |
| 5,584,804 A | 12/1996 | Klatz et al. |
| 5,584,868 A | 12/1996 | Salo et al. |
| 5,587,200 A | 12/1996 | Lorenz et al. |
| 5,589,856 A | 12/1996 | Stein et al. |
| 5,601,609 A | 2/1997 | Duncan |
| 5,601,611 A | 2/1997 | Fayram et al. |
| 5,620,468 A | 4/1997 | Mongeon et al. |
| 5,622,687 A | 4/1997 | Krishnan et al. |
| 5,626,622 A | 5/1997 | Cooper |
| 5,632,267 A | 5/1997 | Hoegnelid et al. |
| 5,634,895 A | 6/1997 | Igo et al. |
| 5,634,899 A | 6/1997 | Shapland et al. |
| 5,649,966 A | 7/1997 | Noren et al. |
| 5,651,378 A | 7/1997 | Matheny et al. |
| 5,654,030 A | 8/1997 | Munshi et al. |
| 5,662,687 A | 9/1997 | Hedberg et al. |
| 5,670,755 A | 9/1997 | Kwon |
| 5,674,251 A | 10/1997 | Combs et al. |
| 5,674,259 A | 10/1997 | Gray |
| 5,683,429 A | 11/1997 | Mehra |
| 5,683,431 A | 11/1997 | Wang |
| 5,687,734 A | 11/1997 | Dempsey et al. |
| 5,690,691 A | 11/1997 | Chen et al. |
| 5,694,945 A | 12/1997 | Ben-Haim |
| 5,697,953 A | 12/1997 | Kroll et al. |
| 5,713,924 A | 2/1998 | Min et al. |
| 5,713,929 A | 2/1998 | Hess et al. |
| 5,713,935 A | 2/1998 | Prutchi et al. |
| 5,720,768 A | 2/1998 | Verboven-Nelissen |
| 5,735,876 A | 4/1998 | Kroll et al. |
| 5,738,096 A | 4/1998 | Ben-Haim |
| 5,738,105 A | 4/1998 | Kroll |
| 5,741,791 A | 4/1998 | Olsen |
| 5,749,906 A | 5/1998 | Kieval et al. |
| 5,755,740 A | 5/1998 | Nappholz |
| 5,777,607 A | 7/1998 | Koolen |
| 5,779,661 A | 7/1998 | Stephen et al. |
| 5,782,876 A | 7/1998 | Flammang |
| 5,782,881 A | 7/1998 | Lu et al. |
| 5,783,951 A | 7/1998 | Inoue et al. |
| 5,790,106 A | 8/1998 | Hirano et al. |
| 5,790,107 A | 8/1998 | Kasser et al. |
| 5,792,198 A | 8/1998 | Nappholz |
| 5,792,208 A | 8/1998 | Gray |
| 5,797,967 A | 8/1998 | KenKnight |
| 5,800,464 A | 9/1998 | Kieval |
| 5,807,234 A | 9/1998 | Bui et al. |
| 5,807,306 A | 9/1998 | Shapland et al. |
| 5,814,079 A | 9/1998 | Kieval |
| 5,825,352 A | 10/1998 | Bisset et al. |
| 5,841,078 A | 11/1998 | Miller et al. |
| 5,854,881 A | 12/1998 | Yoshida et al. |
| 5,861,014 A | 1/1999 | Familoni |
| 5,865,787 A | 2/1999 | Shapland et al. |
| 5,871,506 A | 2/1999 | Mower |
| 5,906,607 A | 5/1999 | Taylor et al. |
| 5,911,223 A | 6/1999 | Weaver et al. |
| 5,913,876 A | 6/1999 | Taylor et al. |
| 5,914,465 A | 6/1999 | Allen et al. |
| 5,919,216 A | 7/1999 | Houben et al. |
| 5,920,309 A | 7/1999 | Bisset et al. |
| 5,927,284 A | 7/1999 | Borst et al. |
| 5,954,761 A | 9/1999 | Machek et al. |
| 5,956,020 A | 9/1999 | D'Amico et al. |
| 5,962,246 A | 10/1999 | Ladner et al. |
| 5,991,649 A | 11/1999 | Garfield et al. |
| 5,995,872 A | 11/1999 | Bourgeois |
| 6,002,594 A | 12/1999 | Ledin et al. |
| 6,006,134 A | 12/1999 | Hill et al. |
| 6,023,640 A | 2/2000 | Ross |
| 6,026,326 A | 2/2000 | Bardy |
| 6,032,074 A | 2/2000 | Collins |
| 6,032,672 A | 3/2000 | Taylor |
| 6,037,882 A | 3/2000 | Levy |
| 6,041,252 A | 3/2000 | Walker et al. |

(56) References Cited

U.S. PATENT DOCUMENTS

| | | |
|---|---|---|
| 6,057,374 A | 5/2000 | Huntington et al. |
| 6,066,163 A | 5/2000 | John |
| 6,067,470 A | 5/2000 | Mower |
| 6,071,305 A | 6/2000 | Brown et al. |
| 6,075,520 A | 6/2000 | Inoue et al. |
| 6,083,249 A | 7/2000 | Familoni |
| 6,086,582 A | 7/2000 | Altman et al. |
| 6,093,167 A | 7/2000 | Houben et al. |
| 6,122,536 A | 9/2000 | Sun et al. |
| 6,128,007 A | 10/2000 | Seybold et al. |
| 6,133,906 A | 10/2000 | Geaghan |
| 6,135,978 A | 10/2000 | Houben et al. |
| 6,136,019 A | 10/2000 | Mower |
| 6,141,586 A | 10/2000 | Mower |
| 6,141,587 A | 10/2000 | Mower |
| 6,151,586 A | 11/2000 | Brown |
| 6,178,351 B1 | 1/2001 | Mower |
| 6,233,484 B1 | 5/2001 | Ben-Haim et al. |
| 6,233,487 B1 | 5/2001 | Mika et al. |
| 6,236,887 B1 | 5/2001 | Ben-Haim et al. |
| 6,239,389 B1 | 5/2001 | Allen et al. |
| 6,243,607 B1 | 6/2001 | Mintchev et al. |
| 6,261,280 B1 | 7/2001 | Houben et al. |
| 6,278,443 B1 | 8/2001 | Amro et al. |
| 6,285,906 B1 | 9/2001 | Ben-Haim et al. |
| 6,292,693 B1 | 9/2001 | Darvish et al. |
| 6,292,704 B1 | 9/2001 | Malonek et al. |
| 6,295,470 B1 | 9/2001 | Mower |
| 6,296,693 B1 | 10/2001 | McCarthy |
| 6,298,254 B2 | 10/2001 | Tamada |
| 6,298,268 B1 | 10/2001 | Ben-Haim et al. |
| 6,317,631 B1 | 11/2001 | Ben-Haim et al. |
| 6,330,476 B1 | 12/2001 | Ben-Haim |
| 6,337,995 B1 | 1/2002 | Mower |
| 6,341,235 B1 | 1/2002 | Mower |
| 6,343,232 B1 | 1/2002 | Mower |
| 6,363,279 B1 | 3/2002 | Ben-Haim et al. |
| 6,381,495 B1 | 4/2002 | Jenkins |
| 6,392,636 B1 | 5/2002 | Ferrari et al. |
| 6,411,847 B1 | 6/2002 | Mower |
| 6,417,846 B1 | 7/2002 | Lee |
| 6,424,864 B1 | 7/2002 | Matsuura |
| 6,433,069 B1 | 8/2002 | Oeltjen et al. |
| 6,449,511 B1 | 9/2002 | Mintchev et al. |
| 6,452,514 B1 | 9/2002 | Philipp |
| 6,463,323 B1 | 10/2002 | Conrad-Vlasak |
| 6,463,324 B1 | 10/2002 | Ben-Haim et al. |
| 6,473,069 B1 | 10/2002 | Gerpheide |
| 6,498,944 B1 | 12/2002 | Ben-Haim et al. |
| 6,504,530 B1 | 1/2003 | Wilson et al. |
| 6,505,745 B1 | 1/2003 | Anderson |
| 6,507,093 B2 | 1/2003 | Kaneda et al. |
| RE38,119 E | 5/2003 | Mower |
| 6,567,700 B1* | 5/2003 | Turcott et al. .................... 607/9 |
| 6,570,557 B1 | 5/2003 | Westerman et al. |
| 6,571,127 B1 | 5/2003 | Ben-Haim et al. |
| 6,572,542 B1 | 6/2003 | Houben et al. |
| 6,583,676 B2 | 6/2003 | Krah et al. |
| 6,587,093 B1 | 7/2003 | Shaw et al. |
| 6,587,721 B1 | 7/2003 | Prutchi et al. |
| 6,600,953 B2 | 7/2003 | Flesler et al. |
| 6,611,258 B1 | 8/2003 | Tanaka et al. |
| 6,612,983 B1 | 9/2003 | Marchal |
| 6,630,123 B1 | 10/2003 | Woltering et al. |
| 6,633,280 B1 | 10/2003 | Matsumoto et al. |
| 6,634,895 B2 | 10/2003 | Agro |
| 6,640,135 B1* | 10/2003 | Salo et al. .................... 607/9 |
| 6,652,444 B1 | 11/2003 | Ross |
| 6,658,297 B2 | 12/2003 | Loeb |
| 6,667,740 B2 | 12/2003 | Ely et al. |
| 6,684,104 B2 | 1/2004 | Gordon et al. |
| 6,690,156 B1 | 2/2004 | Weiner et al. |
| 6,690,963 B2 | 2/2004 | Ben-Haim et al. |
| 6,762,752 B2 | 7/2004 | Perski et al. |
| 6,781,577 B2 | 8/2004 | Shigetaka |
| 6,810,286 B2 | 10/2004 | Donovan et al. |
| 6,853,862 B1 | 2/2005 | Marchal et al. |
| 6,919,205 B2 | 7/2005 | Brighton |
| 6,949,081 B1 | 9/2005 | Chance |
| 7,006,871 B1 | 2/2006 | Darvish et al. |
| 7,027,863 B1* | 4/2006 | Prutchi et al. .................... 607/5 |
| 7,062,318 B2 | 6/2006 | Ben-Haim et al. |
| 7,092,753 B2 | 8/2006 | Darvish et al. |
| 7,167,748 B2 | 1/2007 | Ben-Haim et al. |
| 7,171,263 B2 | 1/2007 | Darvish et al. |
| 7,190,997 B1 | 3/2007 | Darvish et al. |
| 7,218,963 B2 | 5/2007 | Ben-Haim et al. |
| 7,412,289 B2* | 8/2008 | Malonek .................... A61N 1/05 607/119 |
| 7,460,907 B1 | 12/2008 | Darvish et al. |
| 7,840,262 B2 | 11/2010 | Mika et al. |
| 8,958,872 B2 | 2/2015 | Ben-Haim et al. |
| 2002/0010492 A1 | 1/2002 | Donovan et al. |
| 2002/0026141 A1 | 2/2002 | Houben et al. |
| 2002/0052632 A1 | 5/2002 | Ben-Haim et al. |
| 2002/0065455 A1 | 5/2002 | Ben-Haim et al. |
| 2002/0081732 A1 | 6/2002 | Bowlin et al. |
| 2002/0123771 A1 | 9/2002 | Ideker et al. |
| 2002/0161414 A1 | 10/2002 | Flesler et al. |
| 2002/0183682 A1 | 12/2002 | Darvish et al. |
| 2002/0183686 A1 | 12/2002 | Darvish et al. |
| 2003/0018367 A1 | 1/2003 | DiLorenzo |
| 2003/0028221 A1 | 2/2003 | Zhu et al. |
| 2003/0055464 A1 | 3/2003 | Darvish et al. |
| 2003/0055465 A1 | 3/2003 | Ben-Haim et al. |
| 2003/0100889 A1 | 5/2003 | Duverger et al. |
| 2003/0167476 A1 | 9/2003 | Conklin |
| 2003/0181958 A1 | 9/2003 | Doubak, III |
| 2003/0188899 A1 | 10/2003 | Chao et al. |
| 2003/0208242 A1 | 11/2003 | Harel et al. |
| 2003/0211475 A1 | 11/2003 | Roberts |
| 2004/0059393 A1 | 3/2004 | Policker et al. |
| 2004/0095333 A1 | 5/2004 | Morag et al. |
| 2004/0105040 A1 | 6/2004 | Oh et al. |
| 2004/0106954 A1 | 6/2004 | Whitehurst et al. |
| 2004/0138710 A1 | 7/2004 | Shemer et al. |
| 2004/0155871 A1 | 8/2004 | Perski et al. |
| 2004/0158289 A1 | 8/2004 | Girouard et al. |
| 2004/0162595 A1 | 8/2004 | Foley |
| 2004/0172079 A1 | 9/2004 | Chinchoy |
| 2004/0230273 A1 | 11/2004 | Cates et al. |
| 2004/0243190 A1 | 12/2004 | Ben-Haim et al. |
| 2004/0249421 A1 | 12/2004 | Harel et al. |
| 2005/0021101 A1 | 1/2005 | Chen et al. |
| 2005/0033396 A1 | 2/2005 | Ospyka |
| 2005/0095227 A1 | 5/2005 | Rosenzweig et al. |
| 2005/0192542 A1 | 9/2005 | Dev et al. |
| 2005/0277993 A1* | 12/2005 | Mower .................... 607/9 |
| 2006/0036126 A1 | 2/2006 | Ross et al. |
| 2006/0079475 A1 | 4/2006 | Zhang et al. |
| 2006/0085045 A1 | 4/2006 | Harel et al. |
| 2006/0097991 A1 | 5/2006 | Hotelling et al. |
| 2006/0184207 A1 | 8/2006 | Darvish et al. |
| 2007/0027487 A1 | 2/2007 | Mika et al. |
| 2007/0027490 A1 | 2/2007 | Ben-Haim et al. |
| 2007/0088393 A1 | 4/2007 | Ben-Haim et al. |
| 2007/0156177 A1 | 7/2007 | Harel et al. |
| 2007/0171211 A1 | 7/2007 | Perski et al. |
| 2007/0293901 A1 | 12/2007 | Rousso et al. |
| 2008/0058879 A1 | 3/2008 | Ben-Haim et al. |
| 2008/0065159 A1 | 3/2008 | Ben-Haim et al. |
| 2008/0065163 A1 | 3/2008 | Ben-Haim et al. |
| 2008/0065164 A1 | 3/2008 | Ben-Haim et al. |
| 2008/0140142 A1 | 6/2008 | Darvish et al. |
| 2009/0062893 A1 | 3/2009 | Spehr et al. |
| 2009/0292324 A1 | 11/2009 | Rousso et al. |
| 2010/0016923 A1 | 1/2010 | Rousso et al. |
| 2010/0035963 A1 | 2/2010 | Chajut et al. |
| 2013/0096639 A1 | 4/2013 | Ben-Haim et al. |
| 2013/0338425 A1 | 12/2013 | Rousso et al. |
| 2014/0236250 A1 | 8/2014 | Ben-Haim et al. |
| 2015/0157857 A1 | 6/2015 | Ben-Haim et al. |

(56) References Cited

U.S. PATENT DOCUMENTS

| | | | |
|---|---|---|---|
| 2015/0174404 A1 | 6/2015 | Rousso et al. | |
| 2016/0136418 A1 | 5/2016 | Ben-Haim et al. | |

FOREIGN PATENT DOCUMENTS

| | | |
|---|---|---|
| EP | 0156593 | 10/1985 |
| EP | 0250931 | 1/1988 |
| EP | 0314078 | 5/1989 |
| EP | 0481684 | 4/1992 |
| EP | 0 503 839 | 9/1992 |
| EP | 0503839 | 9/1992 |
| EP | 0528751 | 2/1993 |
| EP | 0220916 | 4/1994 |
| EP | 727 241 | 8/1996 |
| EP | 0727241 | 8/1996 |
| EP | 1263498 | 12/2002 |
| EP | 0910429 | 3/2005 |
| GB | 1394171 | 5/1975 |
| GB | 2280377 | 2/1995 |
| JP | 62-112530 | 5/1987 |
| JP | 62-275471 | 11/1987 |
| JP | 62275471 | 11/1987 |
| JP | 04-117967 | 4/1992 |
| JP | 04-282168 | 10/1992 |
| JP | 04-365493 | 12/1992 |
| JP | 436 5493 | 12/1992 |
| JP | 06-169998 | 6/1994 |
| JP | 06-506619 | 7/1994 |
| JP | 07-126600 | 5/1995 |
| JP | 712 6600 | 5/1995 |
| JP | 07-144024 | 6/1995 |
| JP | 08-243176 | 9/1996 |
| RU | 386634 | 6/1973 |
| RU | 553977 | 5/1977 |
| RU | 831131 | 5/1981 |
| RU | 2014844 | 6/1994 |
| RU | 2055606 | 3/1996 |
| RU | 2075980 | 3/1997 |
| RU | 2077273 | 4/1997 |
| RU | 2078547 | 5/1997 |
| WO | WO 91/19534 | 12/1991 |
| WO | WO 92/00716 | 1/1992 |
| WO | WO 92/13592 | 8/1992 |
| WO | WO 93/02743 | 2/1993 |
| WO | WO 93/02745 | 2/1993 |
| WO | WO 93/08874 | 5/1993 |
| WO | WO 93/18820 | 9/1993 |
| WO | WO 94/17855 | 8/1994 |
| WO | WO 95/08316 | 3/1995 |
| WO | WO 96/05768 | 2/1996 |
| WO | WO 96/10358 | 4/1996 |
| WO | WO 96/16696 | 6/1996 |
| WO | WO 97/15227 | 1/1997 |
| WO | WO 97/06849 | 2/1997 |
| WO | WO 97/24983 | 7/1997 |
| WO | WO 97/25098 | 7/1997 |
| WO | WO 97/25101 | 7/1997 |
| WO | WO 97/26042 | 7/1997 |
| WO | WO 97/27900 | 7/1997 |
| WO | WO 97/29682 | 8/1997 |
| WO | WO 97/29684 | 8/1997 |
| WO | WO 97/29700 | 8/1997 |
| WO | WO 97/29701 | 8/1997 |
| WO | WO 97/29709 | 8/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 98/11840 | 3/1998 |
| WO | WO 98/15317 | 4/1998 |
| WO | WO 98/19719 | 4/1998 |
| WO | WO 98/19719 | 5/1998 |
| WO | WO 98/56378 | 12/1998 |
| WO | WO 98/57701 | 12/1998 |
| WO | WO 99/06105 | 2/1999 |
| WO | WO 99/09971 | 3/1999 |
| WO | WO 99/55360 | 4/1999 |
| WO | WO 99/24110 | 5/1999 |
| WO | WO 99/29307 | 6/1999 |
| WO | WO 99/59548 | 11/1999 |
| WO | WO 00/01443 | 1/2000 |
| WO | WO 00/04947 | 2/2000 |
| WO | WO 00/16741 | 3/2000 |
| WO | WO 00/27475 | 5/2000 |
| WO | WO 00/27476 | 5/2000 |
| WO | WO 00/42914 | 7/2000 |
| WO | WO 00/12525 | 9/2000 |
| WO | WO 00/53257 | 9/2000 |
| WO | WO 00/74773 | 12/2000 |
| WO | WO 01/24871 | 4/2001 |
| WO | WO 01/30139 | 5/2001 |
| WO | WO 01/30445 | 5/2001 |
| WO | WO 01/49367 | 7/2001 |
| WO | WO 01/52931 | 7/2001 |
| WO | WO 01/66183 | 9/2001 |
| WO | WO 01/82771 | 11/2001 |
| WO | WO 01/91854 | 12/2001 |
| WO | WO 01/93950 | 12/2001 |
| WO | WO 01/93951 | 12/2001 |
| WO | WO 02/10791 | 2/2002 |
| WO | WO 02/053093 | 7/2002 |
| WO | WO 02/082968 | 10/2002 |
| WO | WO 03/045493 | 5/2003 |
| WO | WO 2004/059393 | 7/2004 |
| WO | WO 2004/070396 | 8/2004 |
| WO | WO 2004/080533 | 9/2004 |
| WO | WO 2005/023081 | 3/2005 |
| WO | WO 2005/087310 | 9/2005 |
| WO | WO 2005/114369 | 12/2005 |
| WO | WO 2006/073671 | 7/2006 |
| WO | WO 2006/087717 | 8/2006 |
| WO | WO 2006/097934 | 9/2006 |
| WO | WO 2006/097935 | 9/2006 |
| WO | WO 2006/119467 | 9/2006 |
| WO | WO 2007/091255 | 8/2007 |

OTHER PUBLICATIONS

King A. et al., The Inotropic Action of Paired Pulse Stimulation in the Normal and Failing Heart: An Experimental Study, Cardiovascular Reseach, vol. 2, Apr. 1968, pp. 122-129.

Dillon, SM., "Optical Recordings in the Rabbit Heart Show that Defibrillation Strength Shocks Prolong the Duration of Depolarization and the Refractory Period" in Circ Res., 69 (3), Sep. 1991, pp. 842-856.

Sweeny RS, et al., Ventricular Refractory Period Extension Caused by Defibrillation Shocks, Circulation, Sep. 1990, vol. 82, No. 3, pp. 965-972.

Gill RJ, et al., abstract of "Refractory Period Extension During Ventricular Pacing at Fibrillatory Pacing Rates", Pacing Clin. Electrophysiol, Mar. 1997, vol. 20, No. 3, pp. 647-653.

Sweeny RJ, et al., abstract of "Refractory Interval After Transcardiac Shocks During Ventricular Fibrillation", Circulation, Dec. 1996, vol. 94, No. 11, pp. 2947-2952.

Sweeney RJ, et al., abstract of "Countershock Strength-Duration Relationship for Myocardial Refractory Period Extension", Acad Emerg. Med., Jan. 1995, vol. 2, No. 1, pp. 57-62.

Dillon, SM, abstract of "Synchronized Repolarization After Defibrillation Shocks. A Possible Component of the Defibrillation Process Demonstration by Optical Recordings in Rabbit Heart", Circulation, May 1992, vol. 85, No. 5, pp. 1865-1878.

Saksena et al., "Dual-Site Atrial Pacing in Atrial Fibrilation", JACC, vol. 28, No. 3, Sep. 1996, pp. 687-694.

Thakor et al., "Effect of Varying Pacing Waveform Shapes on Propagation and Hemodynamics in the Rabbit Heart", The American Journal of Cardiology 79(6A), pp. 36-43. 1997.

Franz, M.R., "Method and Theory of Monophasic Action Potential Recording", Prog. Cardiovasc Dis 33(6), May-Jun. 1991, pp. 347-368.

(56) References Cited

OTHER PUBLICATIONS

Franz, M.R., "Bridging the Gap Between Basic and Clinical Electrophysiology: What Can Be Learned From Monophasic Action Potential Recordings?", J. Cardiovasc Electrophysiol 5(8), Aug. 1994, pp. 699-710.
Bargheer K., et al., "Prolongation of Monophasic Action Potential Duration and the Refractory Period in the Human Heart by Tedisamil, A New Potassium-Blocking Agent", J. Eur Heart 15(10), Oct. 1994, pp. 1409-1414.
Franz, M.R., "Progress in Cardiovascular Diseases: Monophasic Action Potential Symposium, I. Introduction", Prog. Cardiovasc Dis 33(6), May-Jun. 1991, pp. 345-346.
McVeigh E.R., et al., "Noninvasive Measurement of Transmural Gradients in Myocardial Strain with MR Imaging", Radiology 180(3), Sep. 1991, pp. 677, 679-684.
Bers, D.M., Excitation-Contraction Coupling and Cardiac Contractile Force. 1991.
Zipes, D., et al., Cardiac Electrophysiology From Cell to Bedside, 1990, W.B. Saunders Co., Philadelphia 1990.
Josephson, M.E., Clinical Cardiac Electrophysiology: Techniques and Interpretations, 2nd Edition, Lea & Febiger, Philadelphia, 1991.
Wessale, J.L. et al. , "Stroke Volume and Three Phase Cardiac Output Rate Relationship With Ventricular Pacing", Pace 13, May 1990, pp. 673-680.
Wirtzfeld, A., et al., "Physiological Pacing: Present Status and Future Deelopments", PACE 10 Jan.-Feb. 1987, Part I, pp. 41-57.
Talit, U., et al. "The Effect of External Cardiac Pacing on Stroke Volume", PACE 13, May 1990, pp. 598-602.
Webster, John G., ed., Design of Cardiac Pacemakers, IEEE Press, Piscataway, NJ 1995.
Fain, E.S., et al., "Improved Internal Defibrillation Efficacy With a Biphasic Waveform", American Heart Journal, 117(2), Feb. 1989, pp. 358-364.
Fromer, et al., "Ultrarapid Subthreshold Stimulation for Termination of Atrioventricular Node Reentrant Tachycardia", Journal of the American College of Cardiology 20 (Oct. 1992), pp. 879-883.
Knisley, et al. "Prolongation and Shortening of Action Potentials by Electrical Shocks in Frog Ventricular Muscle", American Journal of Physiology 6 (Heart Circ. Physiol. 35, 1994) pp. H2348-H2358.
Antoni, H., et al., "Polarization Effects of Sinusoidal 50 Hz Alternating Current on Membrane Potential of Mammalian Cardiac Fibres",Pflugers Arch. 314, pp. 274-291, 1969.
"http://picuBOOKnet", Apr. 2000,pp. 1-10.
Cooper, W., "Postextrasystolic Potentiation: Do We REally Know What It Means and How to Use It?", Circualation, vol. 88, No. 6, Dec. 1993, pp. 2962-2971.
Foster, A.H., et al., "Acute Hemodyamic Effects of Atrio-Biventricular Pacing in Humans", 1995, The Society of Thoracic Surgeons vol. 59, pp. 294-299.
Cazeau, S., et at., "Multisite Pacing for End-Stage Heart Failure: Early Experience", Pacing and Clincial Electrophysiology vol. 19, Nov. 1996, Part II, pp. 1748-1757.
Yu, et al., "Does Biventricular Pacing Provide Better Cardiac Function Than Univentricular Pacing in Normal Dogs?", Abstract, Heart Failure Society Abstracts-on-Disk, Sep. 13-16, 1998, Boca Raton, Florida, one page.
Auricchio, A., et al., "Acute Pacing of the Left Ventricle is Associated With Largest Hemodynamic Improvements in PTH-CHF Heart Failure Patients", Abstract, Heart Failure Society Abstracts-on-Disk, Sep. 13-16, 1998, Boca Raton, Florida, one page.
Leclercq, C., et al., "Comparative Effects of Permanent Biventricular Pacing in Class III and Class IV Patients", Pacing and Clincial Eelctrophysiology, Apr. 1998, vol. 21, No. 4, Part II, p. 911.
Bakker, P.F., et al., "Beneficial Effects of Biventricular Pacing of Congestive Heart Failure" PACE, vol. 17, Apr. 1994, Part II, one page.
Bakker, P.F., et al. Biventricular Pacing Improves Functional Capacity in Patients With End-Stage Congestive Heart Failure, PACE, Apr. 1995, Part II, one page.

"The Latest Tetralogy of Fallot Discussion With Graphical Support Including Video of Echocardiography and Catheterization", Pediatric ElectrophysiologypicuBOOK ("An On-Line Resource for Pediatric Critical Care") (web address: http://pedsccm.wustl.edu/all-net/english/cardpage/electric/vcsurg/dysrh-8.htm.).
Notice of Non-Compliant Amendment Dated Jul. 15, 2011 From the US Patent and Trademark Office Re. U.S. Appl. No. 11/886,154.
Response Dated Jul. 27, 2011 to Official Action of Apr. 28, 2011 From the US Patent and Trademark Office Re.: U.S. Appl. No. 11/931,889.
Response Dated Jun. 29, 2011 to Notice of Non-Compliant Amendment of Jun. 1, 2011 From the US Patent and Trademark Office Re. U.S. Appl. No. 11/886,154.
Response Dated Jul. 31, 2011 to Official Action of Apr. 14, 2011 From the US Patent and Trademark Office Re.: U.S. Appl. No. 11/932,149.
Sutton et al. "What is a Pacemaker?", The Foundations of Cardiac Pacing, Part I: An Illustrated Practical Guide to Basic Pacing, Chap.4.5: 73-74, 1991.
Webster "Electrodes, Leads, and Biocompatibility", Design of Cardiac Pacemakers, IEEE Press, pp. 141-144, 1995.
Response Dated Dec. 8, 2011 to Office Action of Aug. 3, 2011 From the State Intellectual Property Office (SIPO) of the People's Republic of China Re.: Application No. 200480012687.5.
Response Dated Aug. 1, 2011 to Notice of Non-Compliant Amendment of Jul. 15, 2011 From the US Patent and Trademark Office Re. U.S. Appl. No. 11/886,154.
Translation of Office Action Dated Aug. 3, 2011 From the State Intellectual Property Office (SIPO) of the People's Republic of China Re.: Application No. 200480012687.5.
Communication Pursuant to Article 94(3) EPC Dated Aug. 26, 2011 From the European Patent Office Re. Application No. 06759102.4.
Communication Pursuant to Article 94(3) EPC Dated Aug. 26, 2011 From the European Patent Office Re.: Application No. 05853465.2.
Official Action Dated Oct. 10, 2008 From the US Patent and Trademark Office Re. U.S. Appl. No. 09/980,748.
Official Action Dated Sep. 11, 2009 From the US Patent and Trademark Office Re. U.S. Appl. No. 09/980,748.
Official Action Dated May 21, 2007 From the US Patent and Trademark Office Re. U.S. Appl. No. 09/980,748.
Official Action Dated Dec. 23, 2010 From the US Patent and Trademark Office Re. U.S. Appl. No. 09/980,748.
Official Action Dated Feb. 28, 2008 From the US Patent and Trademark Office Re. U.S. Appl. No. 09/980,748.
Official Action Dated Apr. 29, 2009 From the US Patent and Trademark Office Re. U.S. Appl. No. 09/980,748.
Official Action Dated Aug. 30, 2006 From the US Patent and Trademark Office Re. U.S. Appl. No. 09/980,748.
Official Action Dated Aug. 9, 2011 From the US Patent and Trademark Office Re.: U.S. Appl. No. 11/932,149.
Pre-Appeal Brief Request for Review Dated Aug. 9, 2011 From the US Patent and Trademark Office Re. U.S. Appl. No. 11/933,168.
Official Action Dated Sep. 14, 2011 From the US Patent and Trademark Office Re. U.S. Appl. No. 11/886,154.
Official Action Dated Oct. 11, 2011 From the US Patent and Trademark Office Re.: U.S. Appl. No. 11/919,491.
Official Action Dated Nov. 8, 2011 From the US Patent and Trademark Office Re.: U.S. Appl. No. 11/931,889.
Response Dated Oct. 11, 2011 to Official Action of May 12, 2011 From the US Patent and Trademark Office Re.: U.S. Appl. No. 10/039,845.
Response Dated Aug. 10, 2011 to Official Action of May 13, 2011 From the US Patent and Trademark Office Re. U.S. Appl. No. 11/933,168.
Response Dated Jul. 27, 2011 to Official Action of Apr. 28, 2011 From the US Patent and Trademark Office Re. U.S. Appl. No. 11/931,889.
Official Action Dated Feb. 17, 2012 From the US Patent and Trademark Office Re.: U.S. Appl. No. 11/932,149.
Official Action Dated Feb. 15, 2012 From the US Patent and Trademark Office Re. U.S. Appl. No. 11/802,685.
Notice of Allowance Dated Oct. 10, 2012 From the US Patent and Trademark Office Re.: U.S. Appl. No. 11/802,685.

(56) References Cited

OTHER PUBLICATIONS

Office Action Dated Feb. 21, 2012 From the US Patent and Trademark Office Re. U.S. Appl. No. 10/116,201.
Advisory Action Before the Filing of an Appeal Brief Dated Mar. 22, 2012 From the US Patent and Trademark Office Re. U.S. Appl. No. 11/886,154.
Notice of Allowance Dated May 15 2012 From the US Patent and Trademark Office Re.: U.S. Appl. No. 11/932,149.
Notice of Allowance Dated May 16, 2012 From the US Patent and Trademark Office Re. U.S. Appl. No. 11/886,154.
Notice of Allowance Dated Jun. 20, 2012 From the US Patent and Trademark Office Re. U.S. Appl. No. 11/933,168.
Corrected Notice of Allowability Dated Jul. 13, 2012 From the US Patent and Trademark Office Re. U.S. Appl. No. 11/933,168.
Notice of Allowability Dated Jul. 13, 2012 From the US Patent and Trademark Office Re. U.S. Appl. No. 11/933,168.
Notice of Allowance Dated Jul. 16, 2012 From the US Patent and Trademark Office Re. U.S. Appl. No. 11/931,889.
Notice of Allowance Dated Jul. 18, 2012 From the US Patent and Trademark Office Re.: U.S. Appl. No. 11/931,724.
Official Action Dated Jul. 3, 2012 From the US Patent and Trademark Office Re. U.S. Appl. No. 12/910,943.
Official Action Dated May 10, 2012 From the US Patent and Trademark Office Re. U.S. Appl. No. 10/599,015.
Notice of Allowance Dated Jan. 14, 2011 From the US Patent and Trademark Office Re. U.S. Appl. No. 11/550,560.
Corrected Notice of Allowability Dated Aug. 17, 2012 From the US Patent and Trademark Office Re. U.S. Appl. No. 11/931,724.
Notice of Allowance Dated Aug. 31, 2012 From the US Patent and Trademark Office Re. U.S. Appl. No. 12/910,943.
Official Action Dated Aug. 27, 2012 From the US Patent and Trademark Office Re.: U.S. Appl. No. 11/919,491.
Notice of Non-Compliant Amendment Dated Dec. 12, 2011 From the US Patent and Trademark Office Re. U.S. Appl. No. 11/792,811.
Official Action Dated Jan. 6, 2012 From the US Patent and Trademark Office Re. U.S. Appl. No. 11/933,168.
Official Action Dated Dec. 15, 2011 From the US Patent and Trademark Office Re. U.S. Appl. No. 12/910,943.
Official Action Dated Jan. 18, 2012 From the US Patent and Trademark Office Re. U.S. Appl. No. 11/886,154.
Official Action Dated Dec. 20, 2011 From the US Patent and Trademark Office Re.: U.S. Appl. No. 10/039,845.
Office Action Dated Jan. 18, 2012 From the State Intellectual Property Office (SIPO) of the People's Republic of China Re.: Application No. 200480012687.5 and Its Translation Into English.
Official Action Dated May 29, 2013 From the US Patent and Trademark Office Re. U.S. Appl. No. 13/662,775.
Examination Report Dated Dec. 30, 2013 From the Government of India, Patent Office, Intellectual Property Building Re. Application No. 5571/CHENP/2007.
Hearing Notice in Reference of Application No. 5571/CHENP/2007 Dated Mar. 6, 2014 From the Government of India, Patent Office, Intellectual Property Building Re. Application No. 5571/CHENP/2007.
Notice of Non-Compliant Amendment Dated Jun. 17, 2013 From the US Patent and Trademark Office Re. U.S. Appl. No. 10/039,845.
Examination Report Dated Sep. 17, 2013 From the Government of India, Patent Office, Intellectual Property Building Re. Application No. 5571/CHENP/2007.
Communication to Pursuant to Article 94(3) EPC Dated Sep. 12, 2014 From the European Search Report Re. Application No. 06759102.4.
Applicant-Initiated Interview Summary Dated Dec. 11, 2013 From the US Patent and Trademark Office Re. U.S. Appl. No. 13/970,647.
Applicant-Initiated Interview Summary Dated Dec. 13, 2013 From the US Patent and Trademark Office Re. U.S. Appl. No. 10/116,201.
Knisley et al. "Prolongation and Shortening of Action Potentials by Electrical Shocks in Frog Ventricular Muscle", American Journal of Physiology, 266(6): H2348-H2358, 1994.

Official Action Dated Jul. 29, 2013 From the US Patent and Trademark Office Re. U.S. Appl. No. 10/116,201.
Miledi et al. "Effects of Membrane Polarization on Sarcoplasmic Calcium Release in Skeletal Muscle", Proceedings of the Royal Society of London, Series B, Containing Papers of a Biological Character, 213(1190): 1-13, Sep. 17, 1981. Abstract.
Official Action Dated Sep. 10, 2013 From the US Patent and Trademark Office Re. U.S. Appl. No. 09/980,748.
Official Action Dated Jan. 14, 2014 From the US Patent and Trademark Office Re. U.S. Appl. No. 10/039,845.
Notification of Non-Compliant Appeal Brief (37 CFR 41.37) Dated Sep. 23, 2014 From the US Patent and Trademark Office Re. U.S. Appl. No. 10/039,845.
Official Action Dated Apr. 15, 2014 From the US Patent and Trademark Office Re. U.S. Appl. No. 13/970,647.
U.S. Appl. No. 90/008,688, filed Jun. 15, 2007, Ben Haim.
U.S. Appl. No. 90/008,689, Ben Haim.
U.S. Appl. No. 90/008,707, filed Jun. 7, 2007, Ben Haim.
U.S. Appl. No. 95/000,032, Ben Haim.
Notification of Reexamination Dated Apr. 4, 2014 From the State Intellectual Property Office of the People's Republic of China Re. Application No. 200480012687.5 and Its Translation Into English.
Communication Pursuant to Article 94(3) EPC Dated Jun. 5, 2014 From the European Patent Office Re. Application No. 04719312.3.
Official Action Dated Jul. 1, 2014 From the US Patent and Trademark Office Re. U.S. Appl. No. 10/116,201.
Communication Pursuant to Article 94(3) EPC Dated Sep. 12, 2014 From the European Patent Office Re. Application No. 05853465.2.
Notice of Allowance Dated Oct. 8, 2014 From the US Patent and Trademark Office Re. U.S. Appl. No. 14/181,900.
Amended Request for Ex Parte Reexamination of U.S. Pat. No. 6,317,631 Dated Aug. 20, 2007 From the US Patent and Trademark Office Re.: U.S. Appl. No. 90/008,689.
Communication Pursuant to Article 94(3) EPC Dated Mar. 2, 2009 From the European Patent Office Re.: Application No. 05853465.2.
Communication Pursuant to Article 94(3) EPC Dated Aug. 11, 2010 From the European Patent Office Re. Application No. 99931435.4.
Communication Pursuant to Article 94(3) EPC Dated Jan. 29, 2009 From the European Patent Office Re.: Application No. 04106247.2.
Communication Pursuant to Article 96(2) EPC Dated Mar. 2, 2007 From the European Patent Office Re.: Application No. 97929478.2.
Communication to Pursuant to Article 94(3) EPC Dated Mar. 4, 2009 From the European Search Report Re.: Application No. 06759102.4.
Examination Report Dated Feb. 20, 2013 From the Government of India, Patent Office, Intellectual Property Building Re. Application No. 5571/CHENP/2007.
Examination Report Dated Feb. 27, 2013 From the Government of India, Patent Office, Intellectual Property Building Re. Application No. 2014/CHENP/2008.
Inter Partes Reexamination Communication of U.S. Pat. No. 6,330,476 Dated Sep. 4, 2007 From the US Patent and Trademark Office Re.: U.S. Appl. No. 95/000,032.
International Preliminary Report on Patentability Dated Nov. 15, 2007 From the International Bureau of WIPO Re.: Application No. PCT/US2006/017281.
International Preliminary Report on Patentability Dated Jun. 21, 2007 From the International Bureau of WIPO Re.: Application No. Jun. 21, 2007.
International Preliminary Report on Patentability Dated Sep. 27, 2007 From the international Bureau of WIPO Re.: Application No. PCT/IL2006/000345.
International Search Report and the Written Opinion Dated May 12, 2006 From the International Searching Authority Re.: Application No. PCT/US05/44557.
International Search Report and the Written Opinion Dated Oct. 16, 2006 From the International Searching Authority Re.: Application No. PCT/US06/17281.
Invitation Pursuant to Rule 62a(1) EPC and Rule 63(1) EPC Dated May 5, 2010 From the European Patent Office Re.: Application No. 04719312.3.
Notice of Allowance Dated Jul. 11, 2012 From the US Patent and Trademark Office Re. U.S. Appl. No. 11/550,560.

(56) References Cited

OTHER PUBLICATIONS

Notice of Allowance Dated May 27, 2010 From the US Patent and Trademark Office Re.: U.S. Appl. No. 10/549,216.
Notice of Allowance Dated Dec. 28, 2010 From the US Patent and Trademark Office Re.: U.S. Appl. No. 11/932,064.
Notice of Non-Compliant Amendment Dated Jun. 1, 2011 From the US Patent and Trademark Office Re. U.S. Appl. No. 11/886,154.
Office Action Dated Jan. 8, 2010 From the State Intellectual Property Office (SIPO) of the People's Republic of China Re.: Application No. 200480012687.5 and Its Translation Into English.
Office Action Dated Oct. 12, 2004 From the Israeli Patent Office Re.: Application No. 128955.
Office Action Dated Jul. 13, 2009 From the State Intellectual Property Office of the People's Republic of China Re.: Application No. 200480027283.3 and Its Translation Into English.
Office Action Dated Dec. 15, 2008 From the State Intellectual Property Office (SIPO) of the People's Republic of China Re.: Application No. 200480012687.5 and Its Translation Into English.
Office Action Dated Nov. 25, 2010 From the State Intellectual Property Office (SIPO) of the People's Republic of China Re.: Application No. 200480012687.5 and Its Translation Into English.
Official Action Dated Aug. 1, 2007 From the US Patent and Trademark Office Re.: U.S. Appl. No. 90/008,312.
Official Action Dated Jun. 1, 2009 From the US Patent and Trademark Office Re.: U.S. Appl. No. 10/039,845.
Official Action Dated Dec. 2, 2009 From the US Patent and Trademark Office Re.: Application No. 11/932,149.
Official Action Dated Jan. 3, 2011 From the US Patent and Trademark Office Re.: U.S. Appl. No. 11/932,149.
Official Action Dated Nov. 3, 2009 From the US Patent and Trademark Office Re.: U.S. Appl. No. 11/931,724.
Official Action Dated Feb. 4, 2010 From the US Patent and Trademark Office Re.: U.S. Appl. No. 10/039,845.
Official Action Dated Dec. 5, 2008 From the US Patent and Trademark Office Re.: U.S. Appl. No. 11/550,560.
Official Action Dated Jan. 5, 2010 From the US Patent and Trademark Office Re.: U.S. Appl. No. 11/802,685.
Official Action Dated Nov. 5, 2009 From the US Patent and Trademark Office Re.: U.S. Appl. No. 10/549,216.
Official Action Dated Oct. 5, 2010 From the US Patent and Trademark Office Re.: U.S. Appl. No. 10/039,845.
Official Action Dated Jan. 6, 2010 From the US Patent and Trademark Office Re. U.S. Appl. No. 11/933,168.
Official Action Dated Jan. 6, 2011 From the US Patent and Trademark Office Re.: U.S. Appl. No. 11/931,724.
Official Action Dated Mar. 6, 2009 From the US Patent and Trademark Office Re.: U.S. Appl. No. 11/931,889.
Official Action Dated Mar. 6, 2009 From the US Patent and Trademark Office Re.: U.S. Appl. No. 11/932,064.
Official Action Dated Oct. 6, 2009 From the US Patent and Trademark Office Re.: U.S. Appl. No. 11/550,560.
Official Action Dated Oct. 8, 2009 From the US Patent and Trademark Office Re.: U.S. Appl. No. 10/116,201.
Official Action Dated Jun. 11, 2010 From the US Patent and Trademark Office Re.: U.S. Appl. No. 11/550,560.
Official Action Dated Jun. 11, 2010 From the US Patent and Trademark Office Re.: U.S. Appl. No. 11/932,064.
Official Action Dated May 12, 2011 From the US Patent and Trademark Office Re.: U.S. Appl. No. 10/039,845.
Official Action Dated Sep. 12, 2008 From the US Patent and Trademark Office Re.: U.S. Appl. No. 10/039,845.
Official Action Dated Jan. 13, 2011 From the US Patent and Trademark Office Re.: U.S. Appl. No. 11/931,889.
Official Action Dated May 13, 2011 From the US Patent and Trademark Office Re. U.S. Appl. No. 11/933,168.
Official Action Dated Oct. 13, 2010 From the US Patent and Trademark Office Re.: U.S. Appl. No. 11/919,491.
Official Action Dated Apr. 14, 2011 From the US Patent and Trademark Office Re.: U.S. Appl. No. 11/932,149.
Official Action Dated Sep. 14, 2009 From the US Patent and Trademark Office Re.: U.S. Appl. No. 11/931,889.
Official Action Dated Jul. 15, 2008 From the US Patent and Trademark Office Re.: U.S. Appl. No. 10/116,201.
Official Action Dated Jun. 17, 2010 From the US Patent and Trademark Office Re.: U.S. Appl. No. 10/549,216.
Official Action Dated Jul. 18, 2007 From the US Patent and Trademark Office Re.: U.S. Appl. No. 10/039,845.
Official Action Dated Feb. 21, 2012 From the US Patent and Trademark Office Re. U.S. Appl. No. 10/116,201.
Official Action Dated Jul. 21, 2010 From the US Patent and Trademark Office Re.: U.S. Appl. No. 11/802,685.
Official Action Dated May 21, 2010 From the US Patent and Trademark Office Re. U.S. Appl. No. 10/116,201.
Official Action Dated Mar. 22, 2011 From the US Patent and Trademark Office Re. U.S. Appl. No. 11/886,154.
Official Action Dated Jun. 23, 2009 From the US Patent and Trademark Office Re.: U.S. Appl. No. 10/549,216.
Official Action Dated Jan. 24, 2011 From the US Patent and Trademark Office Re.: U.S. Appl. No. 11/919,491.
Official Action Dated Jun. 26, 2008 From the US Patent and Trademark Office Re.: U.S. Appl. No. 11/536,794.
Official Action Dated Apr. 28, 2011 From the US Patent and Trademark Office Re. U.S. Appl. No. 11/931,889.
Official Action Dated Apr. 28, 2011 From the US Patent and Trademark Office Re.: U.S. Appl. No. 11/931,889.
Official Action Dated Aug. 28, 2009 From the US Patent and Trademark Office Re.: U.S. Appl. No. 11/802,685.
Official Action Dated Aug. 28, 2009 From the US Patent and Trademark Office Re.: U.S. Appl. No. 11/932,064.
Official Action Dated Jun. 28, 2010 From the US Patent and Trademark Office Re.: U.S. Appl. No. 11/931,889.
Official Action Dated Sep. 29, 2010 From the US Patent and Trademark Office Re. U.S. Appl. No. 11/933,168.
Official Action Dated Apr. 30, 2010 From the US Patent and Trademark Office Re.: U.S. Appl. No. 11/931,724.
Official Action Dated Apr. 30, 2010 From the US Patent and Trademark Office Re.: U.S. Appl. No. 11/932,149.
Official Action Dated Aug. 31, 2007 From the US Patent and Trademark Office Re.: U.S. Appl. No. 11/536,794.
Official Action Dated Aug. 31, 2010 From the US Patent and Trademark Office Re.: U.S. Appl. No. 11/550,560.
Request for Ex Parte Reexamination of U.S. Pat. No. 6,363,279—IDS Submitted Dec. 31, 2007 From the US Patent and Trademark Office Re.: U.S. Appl. No. 90/008,688.
Request for Ex Parte Reexamination of U.S. Pat. No. 6,363,279—Notice of Intent to Issue Reexamination Certificate Dated Mar. 18, 2009 From the US Patent and Trademark Office Re.: U.S. Appl. No. 90/008,688.
Request for Ex Parte Reexamination of U.S. Pat. No. 6,363,279—Official Action Dated Jun. 20, 2008 From the US Patent and Trademark Office Re.: U.S. Appl. No. 90/008,688.
Request for Ex Parte Reexamination of U.S. Pat. No. 6,363,279—Order Granting Request Dated Nov. 5, 2007 From the US Patent and Trademark Office Re.: U.S. Appl. No. 90/008,688.
Request for Ex Parte Reexamination of U.S. Pat. No. 6,363,279 Dated Jun. 8, 2007 From the US Patent and Trademark Office Re.: U.S. Appl. No. 90/008,688.
Request for Ex Parte Reexamination of U.S. Pat. No. 6,363,279, Response to Official Action Dated Jun. 20, 2008 Submitted Aug. 20, 2008 From the US Patent and Trademark Office Re.: U.S. Appl. No. 90/008,688.
Request for Ex Parte Reexamination of U.S. Pat. No. 6,236,887—IDS Submitted Oct. 17, 2007 From the US Patent and Trademark Office Re.: U.S. Appl. No. 90/008,707.
Request for Ex Parte Reexamination of U.S. Pat. No. 6,236,887—IDS Submitted Sep. 29, 2008 From the US Patent and Trademark Office Re.: U.S. Appl. No. 90/008,707.
Request for Ex Parte Reexamination of U.S. Pat. No. 6,236,887—Notice of Intent to Issue Ex Parte Examination Certificate Dated Mar. 19, 2009 From the US Patent and Trademark Office Re.: U.S. Appl. No. 90/008,707.

(56) References Cited

OTHER PUBLICATIONS

Request for Ex Parte Reexamination of U.S. Pat. No. 6,236,887—Official Action and IDS Considered Dated Jun. 20, 2008 From the US Patent and Trademark Office Re.: U.S. Appl. No. 90/008,707.
Request for Ex Parte Reexamination of U.S. Pat. No. 6,236,887—Official Action Granting Request for Ex Parte Examination Dated Aug. 17, 2007 From the US Patent and Trademark Office Re.: U.S. Appl. No. 90/008,707.
Request for Ex Parte Reexamination of U.S. Pat. No. 6,236,887 Dated Jun. 13, 2007 From the US Patent and Trademark Office Re.: U.S. Appl. No. 90/008,707.
Request for Ex Parte Reexamination of U.S. Pat. No. 6,298,268—Certificate of Reexamination Issued Mar. 7, 2006, U.S. Appl. No. 90/006,788.
Request for Ex Parte Reexamination of U.S. Pat. No. 6,298,268—IDS Considered Feb. 22, 2005, U.S. Appl. No. 90/006,788.
Request for Ex Parte Reexamination of U.S. Pat. No. 6,298,268—Notice of Intent to Issue Certificate of Reexamination Dated Mar. 29, 2005, U.S. Appl. No. 90/006,788.
Request for Ex Parte Reexamination of U.S. Pat. No. 6,298,268 Dated Oct. 10, 2003, U.S. Appl. No. 90/006,788.
Request for Ex Parte Reexamination of U.S. Pat. No. 6,298,268 Order Granting Request for Ex Parte Reexamination Dated Dec. 19, 2003, U.S. Appl. No. 90/006,788.
Request for Ex Parte Reexamination of U.S. Pat. No. 6,317,631—Amendment in Response to Official Action Dated Jun. 20, 2008, Filed Aug. 20, 2008 From the US Patent and Trademark Office Re.: U.S. Appl. No. 90/008,689.
Request for Ex Parte Reexamination of U.S. Pat. No. 6,317,631—IDS Dated Sep. 26, 2008 From the US Patent and Trademark Office Re.: U.S. Appl. No. 90/008,689.
Request for Ex Parte Reexamination of U.S. Pat. No. 6,317,631—IDS Dated Dec. 31, 2007 From the US Patent and Trademark Office Re.: U.S. Appl. No. 90/008,689.
Request for Ex Parte Reexamination of U.S. Pat. No. 6,317,631—Notice of Intent to Issue Certificate of Reexamination Dated Mar. 18, 2009 From the US Patent and Trademark Office Re.: U.S. Appl. No. 90/008,689.
Request for Ex Parte Reexamination of U.S. Pat. No. 6,317,631—Official Action Dated Jun. 20, 2008, U.S. Appl. No. 90/008,689.
Request for Ex Parte Reexamination of U.S. Pat. No. 6,317,631—Order Granting Reexamination Dated Nov. 5, 2007, U.S. Appl. No. 90/008,689.
Request for Ex Parte Reexamination of U.S. Pat. No. 6,317,631—IDS Dated Jun. 8, 2007, U.S. Appl. No. 90/008,689.
Request for Ex Parte Reexamination of U.S. Pat. No. 6,330,476—IDS Dated May 31, 2006.
Request for Ex Parte Reexamination of U.S. Pat. No. 6,330,476—Comments by 3rd Party Requestor, Response Thereto and Official Action Issued Jul. 16, 2008, U.S. Appl. No. 95/000,032.
Request for Ex Parte Reexamination of U.S. Pat. No. 6,330,476—Communication of Right to Appeal dated Jul. 16, 2008, U.S. Appl. No. 95/000,032.
Request for Ex Parte Reexamination of U.S. Pat. No. 6,330,476—IDS Filed May 4, 2007, U.S. Appl. No. 95/000,032.
Request for Ex Parte Reexamination of U.S. Pat. No. 6,330,476—Official Action by USPTO Issued Mar. 23, 2004, U.S. Appl. No. 95/000,032.
Request for Ex Parte Reexamination of U.S. Pat. No. 6,330,476—Order Granting Request for Reexamination Dated Mar. 23, 2004 From the US Patent and Trademark Office Re.: U.S. Appl. No. 95/000,032.
Request for Ex Parte Reexamination of U.S. Pat. No. 6,330,476 Dated Dec. 31, 2003 From the US Patent and Trademark Office Re.: U.S. Appl. No. 95/000,032.
Request for Ex Parte Reexamination of U.S. Pat. No. 6,463,324—Amendment in Response to Official Action Dated Aug. 1, 2007 Filed Oct. 1, 2007 From the US Patent and Trademark Office Re.: U.S. Appl. No. 90/008,312.
Request for Ex Parte Reexamination of U.S. Pat. No. 6,463,324—Certificate of Reexamination Dated Apr. 29, 2008 From the US Patent and Trademark Office.Re.: U.S. Appl. No. 90/008,312.
Request for Ex Parte Reexamination of U.S. Pat. No. 6,463,324—Official Action—Notice of Intent to Reexamine Dated Jan. 24, 2008 From the US Patent and Trademark Office Re.: U.S. Appl. No. 90/008,312.
Request for Ex Parte Reexamination of U.S. Pat. No. 6,463,324—Official Action Dated Aug. 1, 2007 From the US Patent and Trademark Office Re.: U.S. Appl. No. 90/008,312.
Request for Ex Parte Reexamination of U.S. Pat. No. 6,463,324—Official Action, Interview Summary and References Considered Dated Nov. 6, 2007 From the US Patent and Trademark Office Re.: U.S. Appl. No. 90/008,312.
Request for Ex Parte Reexamination of U.S. Pat. No. 6,463,324 Dated Nov. 1, 2006 From the US Patent and Trademark Office Re.: U.S. Appl. No. 90/008,312.
Summons to Attend Oral Proceedings Pursuant to Rule 115(1) EPC Dated Dec. 22,2008 From the European Patent Office Re.: Applicaton No. 97929480.8.
Supplementary European Search Report and the European Search Opinion Dated Nov. 28, 2008 From the European Patent Office Re.: Applicaton No. 006759102.4.
Supplementary European Search Report and the European Search Opinion Dated Nov. 28, 2008 From the European Patent Office Re.: Application No. 05853465.2.
Supplementary Partial European Search Report Dated Nov. 4, 2010 From the European Patent Office Re. Application No. 04719312.3.
Translation of Notice of Reasons for Rejection Dated Jul. 18, 2006 From the Japanese Patent Office Re.: Application No. 09-529637.
Translation of Notice of Reasons for Rejection Dated Apr. 27, 2010 From the Japanese Patent Office Re.: Application No. 2007-206282.
Translation of Office Action Dated 20 Apr. 2011 From the State Intellectual Property Office (SIPO) of the People's Republic of China Re.: Application No. 200480012687.5.
USPTO Public Print Out of Interference File Content of Interference Dated Apr. 4, 2011 From the US Patent and Trademark Office Re. Interference No. 105,765.
USPTO Public Print Out of Interference File Content of Interference Dated Apr. 4, 2011 From the US Patent and Trademark Office Re. Interference No. 105,768.
Adeghate et al. "Effect of Electrical Field Stimulation on Insulin and Glucagon Secretion From the Pancreas of Normal and Diabetic Rats", Hormone and Metabolic Research, 33(5): 281-289, May 2001. Abstract.
Bergsten et al. "Synchronous Oscillations of Cytoplasmic Ca2+ and Insulin Release in Glucose-Stimulated Pancreatic Islets", The Journal of Biological Chemistry, 269(12): 8749-8753, Mar. 25, 1994.
Blank et al. "Initial Interactions in Electromagnetic Field-Induced Biosynthesis", Journal of Cellular Physiology, 199: 359-363, 2004.
Burfeind et al "The Effects of Mechanical Cardiac Stabilization on Left Ventricular Performance", Europeari Journal of Cardio-Thoracic Surgery, 14: 285-289, 1998.
Butter et al. "Enhanced Inotropic State of the Failing Left Ventricle by Cardiac Contractility Modulation Electrical Signals is Not Associated With Increased Myocardial Oxygen Consumption", Journal of Cardiac Failure, 13(2): 137-142, 2007.
Devedeux et al. "Uterine Electromyography: A Critical Review", American Journal of Obstetric Gynecology, 169(6): 1636-1653, 1993.
Erol-Yilmaz et al. "Reversed Remodelling of Dilated Left Sided Cardiomyopathy After Upgrading from VVIR to VVIR Biventricular Pacing", Europace, 4: 445-449, 2002.
Fromer et al. "Ultrarapid Subthreshold Stimulation for Termination of Atriventricular Node Reentrant Tachycardia", Journal of the American College Cardiology, 20: 879-883, 1992.
Gardner "Natriuretic Peptides: Markers or Modulators of Cardiac Hypertrophy?", Trends in Endocrinology and Metabolism, 14(9): 411-416, Nov. 2003.
Gilmour Jr. et al. "Dynamics of Circus Movement Re-Entry Across Canine Purkinje Fibre-Muscle Junctions", The Journal of Physiology, 476(3): 473-485, 1994.

(56) References Cited

OTHER PUBLICATIONS

Gilmour Jr. et al. "Overdrive Suppression of Conduction at the Canine Purkinje-Muscle Junction", Circulation, 76(6): 1388-1396, 1987.
Gold et al. "Evidence That Glucose 'Marks' Beta Cells Resulting in Preferential Release of Newly Synthesized Insulin", Science, 218(4567): 56-58, Oct. 1, 1982. Abstract.
Gomis et at "Oscillatory Patterns of Electrical Activity in Mouse PancreaticIslets of Langerhans Recorded in Vivo", Pfl?gers Archiv European Journal of Physiology, 432(3): 510-515, 1996.
Gussoni et al. "Dystrophin Expression in the MDX Mouse Restored by Stem Cell Transplantation", Nature, 401(6751): 390-394, 1999.
Hammond et al. "Motor Innervation of the Cricopharyngeus Muscle by the Recurrent Lanryngeal Nerve", Journal of Applied Physiology, JAP, 83: 89-94, 1997.
Highfill et al. "Large-Scale Production of Murine Bone Marrow Cells in an Airlift Packed Bed Bioreactor", Biotechnology and Bioengineering, 50(5): 514-520, 1996.
Hinke et al. "Dipeptidyl Peptidase IV (DPIV/CD26) Degradation of Glucagon. Characterization of Glucagon Degradation Products and DPIV-Resistant Analogs", The Journal of Biological Chemistry, 275(6): 3827-3834, Feb. 11, 2000.
Holst et al. "Nervous Control of Pancreatic Endocrine Secretion in Pigs. I. Insulin and Glucagon Responses to Electrical Stimulation of the Vagus Nerves", Acta Physiologica Scandinavica, 111(1): Jan. 1-7, 1981. Abstract.
Holst et al. "Nervous Control of Pancreatic Endocrine Secretion in Pigs. II. The Effect of Pharmacological Blocking Agents on the Response to Vagal Stimulation", Acta Physiologica Scandinavica, 111(1): 9-14, 1981. Abstract.
Horner et al. "Electrode for Recording Direction of Activation, Conduction Velocity and Monophasic Action Potential of Myocardium", American Journal of Physiology, 272(4): H1917-H1927, 1997. Abstract.
Jaremko et al. "Advances Towards the Implantable Artifical Pancreas for Treatment of Diabetes", Diabetes Care, 21(3): 444-450, 1998.
Kanno et al. "Establishment of a Simple and Practical Procedure Applicable to Therapeutic Angiogenesis", Circulation, 99: 2682-2687, 1999.
Kurose et al. "Glucagon, Insulin and Somatostatin Secretion in Response to Sympathetic Neural Activation in Streptozotocin-Induced Diabetic Rats. A Study With the Isolated Perfused Rat Pancreas In Vitro", Diabetologia, 35(11): 1035-1041, Nov. 1992. Abstract.
Lawo et al. "Electrical Signals Applied During the Absolute Refractory Period. An Investigational Treatment for Advanced Heart Failure in Patients With Normal QRS Duration", Journal of the American College of Cardiology, 46(12): 2229-2236, 2005.
Luiken et al. "Contraction-induced Fatty Acid Translocase/CD36 Translocation in Rat Cardiac Myocytes Is Mediated Through AMP-Activated Protein Kinase Signaling", Diabetes, 52: 1627-1634, 2003.
Magnus et al. "Model of Beta-Cell Mitochondrial Calcium Handling and Electrical Activity. II. Mitochondrial Variables", American Journal of Physiology, Cell Physiology, 274(43): C1174-C1184, 1998.
Meurer et al. "Properties of Native and in Vitro Glycosylated Forms of the Glucogan-Like Peptide-1 Receptor Antagonist Exendin(9-39)", Metabolism: Clinical and Experimental, 48(6): 716-724, Jun. 1999. Abstract.
Misler et al. "Electrophysiology of Stimulus-Secretion Coupling in Human Beta-Cells", Diabetes, 41(10): 1221-1228, Oct. 1992. Abstract.
Nadal et al. "Homologous and Heterologous Asynchronicity Between Identified Alpha-, Beta- and Delta-Cells Within Intact Islets of Langerhans in the Mouse", Journal of Physiology, 517(Pt. 1): 85-93, 1999.
Neelagaru et al. "Nonexcitatory, Cardiac Contractility Modulation Electrical Impulses: Feasibility Study for Advanced Heart Failure in Patients With Normal QRS Duration", Heart Rythm, 3(10): 1140-1147, 2006.
Ohinata et al. "Proadrenomedullin N-Terminal 20 Peptide (PAMP) Elevates Blood Glucose Levels Via Bombesin Receptor in Mice", FEBS Letters, 473(2): 207-211, May 2000. Abstract.
Palti et al. "Islets of Langerhans Generate Wavelike Electric Activity Modulated by Glucose Concentration", Diabetes, 45(5): 595-601, May 1996. Abstract.
Park et al. "Significant Cholinergic Role in Secretin-Stimulated Exocrine Secretion in Isolated Rat Pancreas", American Journal of Physiology, AJP—Gastrointestinal and Liver Physiology, 274(2): G413-G418, Feb. 1998.
Patterson et al. "Therapeutic Angiogenesis: The New Electrophysiology?", Circulation, 99(20): 2614-2616, 1999.
Pokrovsky et al. "Physiology of Man", 1: 82-83, 94, 2: 42, 54.
Porksen et al. "Section 6: Pulsatile and Phasic Insulin Release in Normal and Diabetic Man. Pulsatile Insulin Secretion: Detection, Regulation, and Role in Diabetes", Diabetes, 51(Suppl.1): S245-S254, Feb. 2002.
Rivera et al. "Regulation of Protein Secretion Through Controlled Aggregation in the Endoplasmic Reticulum", Science, 287(5454): 826-830, Feb. 4, 2000. Abstract.
Sakuma et al. "A Model Analysis of Aftereffects of High-Intensity DC Stimulation on Action Potential of Ventricular Muscle", IEEE Transactions on Biomedical Engineering, 45(2): 258-267, 1998.
San Mauro et al. "Nerves of the Heart: A Comprehensive Review With a Clinical Point of View", Neuroanatomy, 8: 28-31, 2009.
Schirra et al. "Exendin(9-39) Amide is an Antagonist of Glucagon-Like Peptide-1(7-36) Amide in Humans", Journal of Clinical Investigation, 101(7): 1421-1430, Apr. 1998.
Schirra et al. "Mechanisms of the Antidiabetic Action of Subcutaneous Glucagon-Like Peptide-1 (17-36) Amide in Non-Insulin Dependent Diabetes Mellitus", Journal of Endocrinology Ltd., 156(1): 177-186, Jan 1998. Abstract.
Serre et al. "Exendin-(9-39) is an Inverse Agonist of the Murine Glucagon-Like Peptide-1 Receptor: Implications for Basal Intracellular Cyclic Adenosine 3',5'-Monophosphate Levels and ?-Cells Glucose Competence", Endocrinology, 139(11): 4448-4454, 1998.
Shah et al. "Impact of Lack of Suppression of Glucagon on Glucose Tolerance in Humans", American Journal of Physiology, AJP—Endocrinology and Metabolism, 277(2 Pt.1): E283-E290, 1999.
Shmit et al. "Physiology of Man", Moscow Medicine, Mir, 1: 78, 1996.
Shuba et al. "Physiology of Vessel Smooth Muscles", Kiev Naukova Dumka, 142: 11-15, 142, 1988.
Singh et al. "Effects of Islet Hormones on Nerve-Mediated and Acetylcholine-Evoked Secretory Responses in the Isolated Pancreas of Normal and Diabetic Rats", International Journal of Molecular Medicine, 1(3): 627-634, Mar. 1998. Abstract.
Soria et al. "Cytosolic Calcium Oscillations and Insulin Release in Pancreatic Islets of Langerhans", Diabetes & Metabolism, 24: 37-40, 1998.
Sukhorukov et al. "The Effect of Electrical Deformation Forces on the Electropermeabilization of Erythrocyte Membranes in Low-and High-Conductivity Media", The Journal of Membrane Biology, 163(3): 235-245, 1998. Abstract.
Sutton et al. "The Foundation of Cardiac Pacing, Part I: An Illustrated Practical Guide to Basic Pacing", The Bakken Research Center Series, Chap.4: 50-59, 1991.
Swerdlow et al. "Cardiovascular Collapse Caused by Electrocardiographically Silent 60-Hz Intracardiac Leakage Current: Implications for Electrical Safety", Circulation, 99: 2559-2564, 1999.
Todd et al. "Subcutaneous Glucagon-Like Peptide I Improves Postprandial Glycaemic Control Over a 3-Week Period in Patients With Early Type 2 Diabetes", Clinical Science, 95: 325-329, 1998.
Valdeolmillos et al. "In Vivo Synchronous Membrane Potential Oscillations in Mouse Pancreatic Beta-Cells: Lack of Co-Ordination Between Islets", Journal of Physiology, 493(1): 9-18, 1996.

(56) References Cited

OTHER PUBLICATIONS

Van Riper et al. "Electrical Field Stimulation-Mediated Relaxation of a Rabbit Middle Cerebral Artery. Evidence of a Cholinergic Endothelium-Dependent Component", Circulation Research, 70(6): 1104-1112, Jun. 1992.
Wang et al. "Islet Amyloid Polypeptide Tonally Inhibits Beta-, Alpha-, and Delta-Cell Secretion in Isolated Rat Pancreatic Islets", American Journal of Physiology, AJP—Endocrinology and Metabolism, 276(1 Pt.1): E19-E24, 1999.
Wright et al. "Structure of Fab hGR-2 F6, A Competitive Antagonist of the Glucagon Receptor", Acta Crystallographica, Section D, Biological Crystallography, 56(Pt.5): 573-580, May 2000. Abstract.
Xue et al. "Neural-Network-Based Adaptive Matched Filtering for QRS Detection", IEEE Transactions on Biomedical Engineering, 39(4): 317-329, 1992. Abstract.
Yonemura et al. "Amelioration of Diabetes Mellitus in Partially Depancreatized Rats by Poly(ADP-Ribose) Synthetase Inhibitors. Evidence of Islet B-Cell Regeneration", Diabetes, 33(4): 401-404, Apr. 1984. Abstract.
Zhou et al. "Prevention of Action Potentials During Extracellular Electrical Stimulation of Long Duration", Journal of Cardiovascular & Electrophysiology, 8(7): 779-789, 1997. Abstract.
Office Action Dated Oct. 21, 2014 From the State Intellectual Property Office (SIPO) of the People's Republic of China Re. Application No. 200480012687.5 and Its Translation Into English. Hearing Notice in Reference of Application 5571/CHENP/2007 Dated Nov. 25, 2014 From the Government of India, Patent Office, Intellectual Property Building Re. Application No. 5571/CHENP/2007.
Official Action Dated Oct. 16, 2013 From the US Patent and Trademark Office Re. U.S. Appl. No. 13/970,647.
Babsky et al. Translation of Physiology of Man, Moscow Medicine, pp. 115, 348-351, 376, Extracts.
Examination Report Dated Jan. 9, 2014 From the Government of India, Patent Office, Intellectual Property Building Re. Application No. 5571/CHENP/2007.
Summons to Attend Oral Proceedings Pursuant to Rule 115(1) EPC Dated Jun. 22, 2015 From the European Patent Office Re. Application No. 05853465.2.
Augello et al. "Cardiac Contractility Modulation by Non-Excitatory Electrical Currents. The New Frontier for Electrical Therapy of Heart Failure", Italian Heart Journal, 5(Suppl.6): 68S-75S, 2004.
Burkhoff et al. "Nonexcitatory Electrical Signals for Enhancing Ventricular Contractility: Rationale and Initial Investigations of an Experimental Treatment for Heart Failure", American Journal of Physiology—Heart and Circulatory Physiology, 288(6): H2550-H2556, Jun. 2005.
Pappone et al. "Cardiac Contractility Modulation by Electric Currents Applied During the Refractory Period in Patients With Heart Failure Secondary to Ischemic or Idiopathic Dilated Cardiomyopathy", The American Journal of Cardiology, 90(12): 1307-1313, Dec. 15, 2002.
Pappone et al. "Electrical Modulation of Cardiac Contractility: Clinical Aspects in Congestive Heart Failure", Heart Failure Reviews, 6(1): 55-60, Jan. 2001.
Pappone et al. "First Human Chronic Experience With Cardiac Contractility Modulation by Nonexcitatory Electrical Currents for Treating Systolic Heart Failure: Mid-Term Safety and Efficacy Results From a Multicenter Study", Journal of Cardiovadcular Electrophysiology, 15(4): 418-427, Apr. 2004.
Sabbah et al. "Treating Heart Failure With Cardiac Contractility Modulation Electrical Signals", Current Heart Failure Reports, 3(21): 21-24, 2006.
Stix et al. "FT Chronic Electrical Stimulation During the Absolute Refractory Period of the Myocardium Improves Severe Heart Failure", European Heart Journal, 3: 1-6, Feb. 2004.
Communication Under Rule 71(3) EPC Dated Mar. 4, 2015 From the European Patent Office Re. Application No. 04719312.3.
Official Action Dated Apr. 28, 2015 From the US Patent and Trademark Office Re. U.S. Appl. No. 14/621,988.

Office Action Dated Apr. 30, 2015 From the State Intellectual Property Office (SIPO) of the People's Republic of China Re. Application No. 200480012687.5 and Its Translation Into English.
Summons to Attend Oral Proceedings Pursuant to Rule 115(1) EPC Dated May 8, 2015 From the European Search Report Re. Application No. 06759102.4.
Restriction Official Action Dated Mar. 17, 2016 From the US Patent and Trademark Office Re. U.S. Appl. No. 11/792,811.
Communication Pursuant to Article 94(3) EPC Dated Nov. 11, 2015 From the European Patent Office Re. Application No. 04106247.2.
Communication Pursuant to Article 94(3) EPC Dated Nov. 10, 2015 From the European Patent Office Re. Application No. 01928181.5.
Communication Pursuant to Article 94(3) EPC Dated Jun. 17, 2008 From the European Patent Office Re. Application No. 01928181.5.
Notice of Allowance Dated May 6, 2016 From the US Patent and Trademark Office Re. U.S. Appl. No. 14/641,480.
Supplementary Partial European Search Report Dated Sep. 6, 2006 From the European Patent Office Re. Application No. 01928181.5.
Antman et al. "Treatment of 150 Cases of Life-Threatening Digitalis Intoxication With Digoxin-Specific Fab Antibody Fragments", Circulation, 81(6): 1744-1752, Jun. 1990.
Antoni et al. "Polarization Effects of Sinusoidal 50-Cycle Alternating Current on Membrane Potential of Mammalian Cardiac Fibres", Pfl?gers Archiv European Journal of Physiology, 314(4): 274-291, 1970. Abstract.
Bach "Tach Arrhythmia Detection", Implantable Cardiovascular Defibrilator Therapy: The Engineering—Clinical Interface, Kluwer Academic Publishers, Chap. 15: 303-323, 1997.
Bakker et al. "Beneficial Effects of Biventricular Pacing of Congestive Heart Failure", Pace, 17(Part II): 318, 1994.
Bakker et al. "Biventricular Pacing Improves Functional Capacity in Patients with End-Stage Congestive Heart Failure", Pace, 17(Pt. 11): 1.P, 1995.
Bargheer et al. "Prolongation of Monophasic Action Potential Duration and the Refractory Period in the Human Heart by Tedisamil, A New Potassium-Blocking Agent", Journal European Heart, 15(10): 1409-1414, 1994.
Borst et al. "Coronary Artery Bypass Gratting Without Cardiopulomonary Bypass and Without Interuption of Native Coronary Flow Using a Novel Anastomosis Site Restraining Device (Octupus)", Journal of the American College of Cardiology, 27(6): 1356-1364, 1996.
Bronzino "Biomedical Engineering Handbook", IEEE Press/CRC Press, Chap. 82.5: 1288, 1995.
Brumwell et al. "The Amplifier Sensing the Depolarization", Implantable Cardioverter Defibrillator Therapy: The Engineering-Clinical Interface, Kluwer Academic Publishers, Chap.14: 275-302, 1997.
Cano et al. "Dose-Dependent Reversal of Dixogin-Inhibited Activity of an In-Vitro Na+K+ATPase Model by Digoxin-Specific Antibody", Toxicology Letters, 85(2): 107-1011, 1996.
Cazeau et al. "Multisite Pacing for End-Stage Heart Failure: Early Experience", Pacing and Clinical Electrophysiology, 19(11): 1748-1757, 1996. Abstract.
Cheng et al. "Calcium Sparks: Elementary Events Underlying Excitation-Contraction Coupling in Heart Muscle", Science, 262(5134): 740-744, 1993. Abstract.
Cooper "Postextrasystolic Potention. Do We Really Know What It Means and How to Use It?", Circulation, 88: 2962-2971, 1993.
Coulton et al. "Magnetic Fields and Intracellular Calcium; Effects on Lymphocytes Exposed to Conditions for 'Cyclotron Resonance' ", Phys. Med. Biol., 38: 347-360, 1993, Abstract.
Dillon "Optial Recordings in the Rabbit Heart Show That Defibrillation Strength Shocks Prolong the Duration of Depolarization and the Refractory Period", Circulation Research, 69: 842-856, 1991.
Dillon "Synchronized Repolarization After Defibrillation Shocks. A Possible Component of the Defibrillation Process Demonstration by Optical Recordings in Rabbit Heart", Circulation, 85(5): 1865-1878, 1992.
Fain et al. "Improved Internal Defibrillation Efficacy With a Biphasic Waveform", American Heart Journal, 117(2): 358-364, 1989. Abstract.

(56) References Cited

OTHER PUBLICATIONS

Fleg et al. "Impact of Age on the Cardiovasvular Response to Dynamic Upright Exercise in Healthy Men and Women", Journal of Applied Physiology, 78: 890-900, 1995. Abstract.
Fleischhauer et al. "Electrical Resistances of Interstitial and Microvascular Space as Determinants of the Extracellular Electrical Field and Velocity of Propagation in Ventricular Myocardium", Circulation, 92: 587-594, 1995.
Foster et al. "Acute Hemodynamic Effects of Atrio-Biventricular Padng in Humans", The Society of Thoracic Surgeons, 59: 294-300, 1995.
Franz "Bridging the Gap Between Basic Clinical Electrophysiology: What Can Be Learned From Monophasic Action Potential Recordings?", Journal Cardiovasc Electrophysiology, 5(8): 699-710, 1994, Abstract.
Franz "Method and Theory of Monophasic Action Potential Recording", Progress in Cardiovascular Diseases, 33(6): 347-368, 1991. Abstract.
Franz "Monophasic Action Potential Symposium, I. Introduction", Progress in Cardiovascular Diseases, 33(6): 345-346, 1991.
Fu et al. "System Identification of Electrically Coupled Smooth Music Cells: The Passive Electrically Coupled Smooth Muscle Cells: The Passive Electrical Properties", IEEE Transactions on Biomedical Engineering, 38(11): 1130-1140, 1991. Abstract.
Gill et al. "Refractory Period Extension During Ventricular Pacing at Fibrillatory Pacing Rates", Pacing and Clinical Elctrophysiology, 20(3): 647-653, 1997. Abstract.
Guidant Guidant Product Catalog, 2 P., 2001.
Ham et al. "Classification of Cardiac Arrhythmias Using Fuzzy Artmap", IEEE Transactions on Biomedical Engineering, 43(4): 425-429, 1996, Abstract.
Hardage el al, "Anti-Tachycardia Pacing and Cardioversion", Developments in Cardiovascular Medicine, Kluwer Academic Publishers, 188: 325-342, 1997.
Hoffman et al. "Effects of Postextrasystolic Potentiation on Normal and Failing Hearts", Bulletin of the New York Academy of Medicine, 41(5): 498-534, 1965.
Josephson "Clinical Cardiac Electrophysiology: Techniques and Interpertations", Lea & Febiger, 2nd Ed., 2 P., 1991.
King et al. "The Inotropic Action of Paired Pulse Stimulation in the Normal and Failing Heart: An Experimental Study", Cardiovascular Research, 2: 122-129, 1968.
Knisley et al. "Effect of Field Stimulation on Cellular Repolarization in Rabbit Myocardium. Implications for Reentry Induction", Circulation Research, 70(4): 707-715, Apr. 1992.
Koller et al. "Relation Between Repolarization and Refractoriness During Programmed Electrical Stimulation in the Human Right Ventricle", Circulation, 91(9): 2378-2384, 1995.
Langberg et al. "Identification of Ventricular Tachycardia With Use of the Morphology of the Endocardial Electrogram", Circulation, 77(6): 1363-1369, 1988.
Lindstroem et al. "Intracellular Calcium Oscillations in a T-Cell Line After Exposure to Extremely-Low-Frequency Magnetic Fields With Variable Frequencies and Flux Densities", Bioelectromagnetics, 16(1): 41-47, 1995. Abstract.
Loginov "[Accumulation of Calcium Ions in Myocardial Sarcoplasmic Reticulum of Restrained Rats Exposed to the Pulsed Electromagnetic Field]", Aviakosmicheskaia i Ekologicheskaia Meditsina (Aerospace and Environmental Medicine), 26(2): 49-51, Mar.-Apr. 1992. Abstract.
Loginov et al. "Effects of an Impulse Electromagnetic Field on Calcium Ion Accumulation in the Sarcoplasmic . . . ", Kosm. Biol. Aviakosm. Med., 15: 51-53, 1991. Abstract.
Lubart et al. "Effect of Light on Calcium Transport in Bull Sperm Cells", Journal of Photochemistry and Photobiology B, Biology, 15(4): 337-341, Sep. 15, 1992. Abstract.
Matheny et al. "Vagus Nerve Stimulation as a Method to Temporarily Slow or Anrest the Heart", Annals of Thoracic Surgery, 63(6 Suppl.): S28-29, 1997. Abstract.

McVeigh et al. "Noninvasive Measurement of Transmural Gradients in Myocardial Strain With MR Imaging", Radiology, 180(3): 677-684, 1991.
Mercando et al. "Automated Detection of Tachycardias by Antitachycardia Devices", Cardiac Electrophysiology: From Cell to Bedside, Chap.100: 943-948, 2004.
Merck "The Merck Manual", 16th Ed, Section 3, 1992.
Moran et al. "Digoxin-Specific Fab Fragments Impair Renal Function in the Rat", Journal of Pharmacy and Pharmacology, 46(10): 854-856, 1994, Abstract.
Morse et al. "A Guide to Cardiac Pacemakers, Defibrillators and Related Products", Droege Computing Services, Inc., vol. I, Nov. 19, 1996.
Nannini et al. "Muscle Recruitment With Intrafascicular Electrodes", IEEE Transactions on Biomedical Engineering, 38: 769-776, 1991. Abstract.
Paul et al. "Automatic Recognition of Ventricular Arrhythmias Using Temporal Electrogram Analysis", PACE, 14: 1265-1273, 1991.
Pediatric Electrophysiology "The Latest Tetralogy of Fallot Discussion With Graphical Support Including Video of Echocardiography and Catherizartion", Pediatric Electrophysiologypicu Book.
Pumir et al. "Control of Rotating Waves in Cardiac Muscle: Analysis of the Effect of Electric Fields", Proceedings of the Royal Society B: Biological Sciences, 257(1349): 129-134, 1994. Abstract.
Ranjan et al. "Electrical Stimulation of Cardiac Myocytes", Annals of Biomedical Engineering, 23(6): 812-821, 1995, Abstract.
Saksena et al. "Prevention of Recurrent Atrial Fibrillation With Chronic Dual-Site Right Atrial Pacing", Journal of the American College of Cardiology, 28(3): 687-694, 1996, Abstract.
Schwartz et al. "Exposure of Frog Hearts to CW or Amplitude-Modified VHF Fields: Selective Efflux of Calcium Ions at 16 Hz", Bioelectromagnetics, 11(4): 349-358, 1990, Abstract.
Shumaik et al. "Oleander Poisoning: Treatment With Digoxin-Specific Fab Antibody Fragments", Annals of Emergency Medicine, 17(7): 732-735, 1988.
Skale et al. "Inhibition of Premature Ventricular Extrastimuli by Subthreshold Conditioning Stimuli", Journal of the American College of Cardiology, 6: 133-140, 1985. Abstract.
Solomonow et al. "Control of Muscle Contractile Force Through Indirect High-Frequency Stimulation", American Journal of Physical Medicine, 62(2): 71-82, Apr. 1983. Abstract.
Stevenson et al. "Electrophysiologic Characteristics of Ventricular Tachycardia or Fibrillation in Relation to Age of Myocardial Infarction", The American Journal of Cardiology, 57(6): 387-391, Feb. 15, 1986. Abstract.
Supino "The System", Implantable Cardioverter Defibrillator Therapy: The Engineering-Clinal Interface, Kluwer Academic Publishers, Chap.8: 163-172, 1997.
Sweeny et al. "Countershock Strength-Duration Relationship for Myocardial Refractory Period Extension", Academic Emergency Medicine, 2(1): 57-62, 1995, Abstract.
Sweeny et al. "Refractory Interval After Transcardiac Shocks During Ventricular Fibrillation", Circulation, 94(11): 2947-2952, 1996.
Sweeny et al. "Ventricular Refractory Period Extension Caused by Defibrillation Shocks", Circulation, 82(3): 965-972, 1990.
Talit et al. "The Effect of External Cardiac Pacing on Stroke Volume", PACE, 13(5): 598-602, May 1990. Abstract.
Taniguchi et al. "Inhomogeneity of Cellular Activation Time and Vmax in Normal Myocardial Tissue Under Electrical Field Stimulation", American Journal of Physiology—Heart and Circulatory Physiology, 267: H694-H705, 1994, Abstract.
Thakor et al. "Effect of Varying Pacing Waveform Shapes on Propagation and Hemodynamics in the Rabbit Heart", The Americal Journal of Cardiology, 79(6A): 36-43, 1997. Abstract.
Tsang "Electroporation of Cell Membranes", Biophysical Journal, 60: 297-306, 1991.
Verrier et al. "Electrophysiologic Basis for T Wave Alternans as an Index of Vulnerability to Ventricular Fibrillation", Journal of Cardiovascular Electrophysiology, 5(5): 445-461, 1994. Abstract.

(56) References Cited

OTHER PUBLICATIONS

Webster "Design of Cardiac Pacemakers", IEEE Press, p. xi-xiii, 1995.
Wessale et al. "Stroke Volume and the Three Phase Cardiac Output Rate Relationship With Ventricular Pacing", PACE, 13: 673-680, 1990.
Windle et al. "Subthreshold Conditioning Stimuli Prolong Human Ventricular Refractoriness", American Journal of Cardiology, 57(6): 381-386, 1986. Abstract.
Wirtzfeld et al. "Physiological Pacing: Present Status and Future Developments", PACE, 10(Part I): 41-57, Jan. 1987. Abstract.
Yokoyama "The Phase of Supernormal Excitation in Relation to the Strength of Subthreshold Stimuli", Japanese Heart Journal, 17(3): 315-325, May 1976.
Zipes et al. "Cardiac Electrophysiology—From Cell to Bedside", Saunders Co., 4th Ed., 2004. Abstract.
Official Action Dated Sep. 15, 2016 From the US Patent and Trademark Office Re. U.S. Appl. No. 14/941,790.
Official Action Dated Sep. 19, 2016 From the US Patent and Trademark Office Re. U.S. Appl. No. 11/792,811.
Applicant-Initiated Interview Summary Dated Nov. 28, 2012 From the US Patent and Trademark Office Re.: U.S. Appl. No. 11/919,491.
U.S. Office Action issued Sep. 29, 2010—U.S. Appl. No. 11/933,168.

* cited by examiner

SIGNAL DELIVERY THROUGH THE RIGHT VENTRICULAR SEPTUM

CROSS-REFERENCES TO RELATED APPLICATIONS

The present application is a continuation-in-part of U.S. Ser. No. 10/672,385, filed Sep. 26, 2003, which is:

a continuation of commonly assigned U.S. Ser. No. 09/848,535, filed May 3, 2001, now abandoned, which is based upon commonly assigned U.S. 60/202,382, filed May 4, 2000;

a continuation-in-part of co-pending, commonly assigned U.S. Ser. No. 10/188,726, filed Jul. 2, 2002, which is a continuation of commonly assigned U.S. Ser. No. 09/254,903, filed Mar. 12, 1999, now U.S. Pat. No. 6,415,178, which is a U.S. National Phase Patent Application of PCT/IL97/00233, filed Jul. 9, 1997, which is based upon U.S. 60/026,392, filed Sep. 16, 1996, and Israeli Patent Application 119,261, filed Sep. 17, 1996; and a continuation-in-part of co-pending, commonly assigned U.S. Ser. No. 10/039,845, filed Oct. 23, 2001, which is a continuation of U.S. Ser. No. 09/563,544, filed May 1, 2000, now U.S. Pat. No. 6,363,279, which is a continuation of U.S. Ser. No. 09/101,723, filed Aug. 13, 1998, now U.S. Pat. No. 6,317,631, which is a U.S. National Phase filing of PCT/IL97/00012, filed Jan. 8, 1997, which is based upon U.S. 60/009,769, filed Jan. 11, 1996, U.S. 60/011,117, filed Feb. 5, 1996, U.S. 60/026,392, filed Sep. 16, 1996, U.S. Ser. No. 08/595,365, filed Feb. 1, 1996, now U.S. Pat. No. 5,738,096, and Israeli Patent Application No. 119,261, filed Sep. 17, 1996.

All of the above references are incorporated herein by reference in their entirety.

FIELD OF THE INVENTION

The present invention relates generally to invasive devices and methods for treatment of the heart, and specifically to devices and methods for improving cardiac performance.

BACKGROUND OF THE INVENTION

The heart requires precise coordination of its mechanical and electrical behavior to function optimally. The human body normally regulates cardiac output in response to body needs by changing the heart rate, as during physical exercise, and/or by adapting the stroke volume. Under pathological conditions, however, some of the normal regulatory mechanisms may be damaged. For example, heart tissue damaged due to myocardial infarct typically cannot sustain normal pumping function. Alternatively or additionally, normal electrical signals are not generated, or are impaired in their propagation, such that cardiac output and cardiac efficiency (stroke work divided by oxygen consumption) are correspondingly compromised. Standard pacemakers known in the art are able to control the rate of the heart, e.g., to accelerate the heart rate after detecting bradycardia, but are not able to increase contraction strength over the long-term without producing adverse side-effects.

US Patent Application Publication 2002/0055764 to Malonek et al., which is assigned to the assignee of the present patent application and is incorporated herein by reference, describes a lead for modifying the activity of a tissue, particularly the heart. Electrodes are provided for performing sensing and/or signal delivery functions. A control unit controls the parameters of the electric field provided by signal delivery electrodes to prevent the generation of a propagation action potential in the tissue.

PCT Patent Publication WO 97/25098, to Ben-Haim et al., entitled "Electrical muscle controller," and the corresponding U.S. patent application Ser. No. 09/101,723, which are assigned to the assignee of the present patent application and are incorporated herein by reference, describe methods for modifying the force of contraction of at least a portion of a heart chamber by applying a non-excitatory electric signal to the heart at a delay after electrical activation of the portion. The non-excitatory signal is such as does not induce action potentials in cardiac muscle cells, but rather modifies the cells' response to the activation. In the context of the present patent application, the use of such a non-excitatory signal is referred to as Excitable-Tissue Control (ETC). The non-excitatory signal may be applied in combination with a pacemaker or defibrillator, which applies an excitatory signal (i.e., pacing or defibrillation pulses) to the heart muscle.

PCT Patent Publication WO 98/10832, to Ben-Haim et al., entitled "Cardiac output enhanced pacemaker," and the corresponding U.S. patent application Ser. No. 09/254,900, which are assigned to the assignee of the present patent application and incorporated herein by reference, describe a pacemaker that gives cardiac output enhancement. This pacemaker applies both excitatory (pacing) and non-excitatory (ETC) electrical stimulation pulses to the heart. By applying non-excitatory pulses of suitable strength, appropriately timed with respect to the heart's electrical activation, the contraction of selected segments of the heart muscle can be increased or decreased, thus increasing or decreasing the stroke volume of the heart.

The following patent references are incorporated herein by reference: U.S. Pat. No. 6,714,823, WO 99/55412, U.S. Pat. No. 6,064,906, WO 98/41144, U.S. Pat. No. 5,772,604, WO 97/49143, and U.S. Pat. No. 5,350,419.

SUMMARY OF THE INVENTION

It is an object of some aspects of the present invention to provide improved methods and apparatus for stimulating cardiac tissue.

It is a finer object of some aspects of the present invention to provide improved methods and apparatus for enhancing cardiac performance.

It is still a further object of some aspects of the present invention to provide improved methods and apparatus for increasing cardiac output.

In preferred embodiments of the present invention, an electrical cardiac stimulator for improving the performance of the heart of a human subject applies an Excitable-Tissue Control (ETC) signal to the interventricular septum via one or more electrodes passed by catheter into the right ventricle. Preferably, but not necessarily, at least one electrode is screwed or otherwise fixed to the septum, and delivers the ETC signal during a refractory period of excitable tissue of the septum, so as to modify a characteristic of the mechanical behavior thereof.

An ETC signal is an example of a "refractory-period signal," which is a signal applied to a cardiac site during the refractory period of the cardiac site.

It is noted that these embodiments of the present invention simplify the procedure of applying electrical signals to modulate cardiac contraction. It is known in the art to apply pacing signals to the left ventricle by the difficult procedure of passing a catheter through the coronary veins. It is also known in the art to make an incision in a patients chest so as to implant pacing electrodes on the heart. It is further known in the art to pace both ventricles via an electrode placed on the interventricular septum, whereby pacing pulses generated by the electrode cause an activation wave to propagate through the septum, through normal conduction pathways of the heart. These prior art techniques differ from preferred embodiments of the present invention in that the prior art is directed towards stimulating one or both ventricles to contract, while these embodiments of the present invention provide means for modulating the mechanical behavior of the septum itself, substantially without inducing new action potentials.

Typically, each electrode conveys a particular waveform to the septum, which may differ in certain aspects from the waveforms applied to other electrodes. The particular waveform to be applied to each electrode is preferably determined by a control unit, initially under the control of a physician during a calibration period of the unit. Further preferably, the cardiac stimulator (or elements thereof) is implanted in the patient in a manner similar to that used to implant pacemakers or defibrillators known in the art. After the initial calibration period, the unit is generally able to automatically modify the waveforms as needed to maintain a desired level of performance of the stimulator. In many applications, standard pacing, cardioversion, and/or defibrillation capabilities are additionally incorporated into the stimulator.

In a preferred embodiment, one or more mechanical sensors, e.g., force transducers, strain gauges, pressure gauges, and/or motion sensors, are positioned in a vicinity of the heart, and are coupled to send mechanical-sensor signals to the control unit indicative of aspects of the heart's functioning. Alternatively or additionally, one or more physiological sensors, e.g., for measuring mixed venous oxygen saturation (SvO2) or thoracic electrical impedance, send physiological-sensor signals to the control unit. The various sensor signals serve as feedback to enable the control unit to iteratively adjust the ETC signal applied to the septum, so as to cause the sensor signals to converge to desired values. Alternatively or additionally, other sensors, such as sensing electrodes, blood pressure sensors, or flow tranducers, are coupled to the heart or elsewhere on the patient's body, and send signals to the control unit which are used in determining modifications to parameters of the energy applied to the heart.

Further alternatively or additionally, the control unit analyzes the sensor signals to detect an onset of arrhythmia, for example, an ectopic heartbeat. In this case, the control unit preferably modifies or terminates application of the ETC signal responsive to the detection.

There is therefore provided, in accordance with a preferred embodiment of the present invention, a method for applying a signal to a heart of a human subject, including applying an Excitable-Tissue Control (ETC) signal to a site on the right ventricular septum of the heart.

Typically, applying the ETC signal includes configuring the signal to be capable of modifying contractility of a portion of the heart. For example, configuring the ETC signal may include configuring the signal to be capable of modifying contractility of the left ventricle of the heart, the septum, or the right ventricle of the heart.

Preferably, configuring the ETC signal includes configuring the signal to be capable of increasing contractility of the portion of the heart. Alternatively, configuring the ETC signal includes configuring the signal to be capable of decreasing contractility of the portion of the heart. In a preferred embodiment, configuring the ETC signal to be capable of decreasing the contractility includes configuring the signal to be capable of decreasing contractility of the septum.

For some applications, applying the ETC signal includes applying a series of biphasic pulses. Alternatively or additionally, applying the ETC signal includes applying a series of generally square pulses. Further alternatively or additionally, applying the ETC signal includes applying a series of pulses at a rate greater than about 50 Hz. Still further alternatively or additionally, applying the ETC signal includes applying a series of pulses at a rate less than about 100 Hz.

Preferably, applying the ETC signal includes applying a series of pulses which are greater than about 8 mA. For some applications, applying the ETC signal includes applying a series of pulses which are greater than about 10 mA.

In a preferred embodiment of the present invention, applying the ETC signal includes applying the ETC signal to a site at or adjacent to an intersection of the septum and the right ventricular free wall.

There is also provided, in accordance with a-preferred embodiment of the present invention, apparatus for applying a signal to a heart of a human subject, including:

a set of one or more electrodes, adapted to be coupled to the right ventricular septum of the heart; and a control unit, adapted to drive the electrode set to apply an Excitable-Tissue Control (ETC) signal to the septum.

There is additionally provided, in accordance with an embodiment of the invention, a method for use with a human subject having a heart, including:

accessing a cardiac site via a vena cava of the subject; and alleviating heart failure of the subject by applying to the cardiac site, during a refractory period of the site, a refractory-period signal that affects a left ventricle of the heart.

In an embodiment, applying the refractory-period signal includes applying an excitatory-tissue control (ETC) signal.

In an embodiment, applying the refractory-period signal includes configuring the refractory-period signal to increase cardiac output of the heart.

In an embodiment, accessing the cardiac site includes accessing a plurality of cardiac sites via the vena cava, and applying the signal to the cardiac site includes applying energy to each of the cardiac sites.

In an embodiment, accessing the cardiac site via the vena cava includes guiding an electrode through a right ventricle of the subject.

In an embodiment, applying the signal includes applying the signal during a bipolar signal application period.

In an embodiment, applying the signal includes applying the signal during a monopolar signal application period.

In an embodiment, applying the refractory-period signal includes applying a series of biphasic pulses.

In an embodiment, applying the refractory-period signal includes applying a series of generally square pulses.

In an embodiment, applying the refractory-period signal includes applying a series of pulses at a rate greater than 50 Hz.

In an embodiment, applying the refractory-period signal includes applying a series of pulses at a rate less than 100 Hz.

In an embodiment, applying the refractory-period signal includes applying a series of pulses at a rate between 50 Hz and 100 Hz.

In an embodiment, applying the refractory-period signal includes applying the refractory-period signal to a site at or adjacent to an intersection of an interventricular septum and a right ventricular free wall of the heart.

In an embodiment, applying the refractory-period signal includes chronically applying the refractory-period signal.

In an embodiment, chronically applying includes configuring the refractory-period signal to engender long-term alleviation of the heart failure.

In an embodiment, the method includes applying a pacing signal to the site during an excitatory period of a cardiac cycle, and applying the refractory-period signal includes applying the refractory-period signal during a refractory period of the same cardiac cycle.

In an embodiment, applying the pacing signal includes applying the pacing signal with no delay following applying the refractory-period signal.

In an embodiment, applying the pacing signal includes applying the pacing signal following a delay after applying the refractory-period signal.

In an embodiment, applying the refractory-period signal includes applying a plurality of pulses that are greater than 1 mJ.

In an embodiment, applying the plurality of pulses includes applying a plurality of pulses that are greater than 5 mJ.

In an embodiment, the method includes sensing electrical activity of the heart at a sensing site, and applying the refractory-period signal in response to the sensing.

In an embodiment, the sensing site is different from the cardiac site, and sensing the electrical activity includes sensing at the sensing site that is different from the cardiac site.

In an embodiment, the sensing site includes the cardiac site, sensing includes sensing using an electrode, and applying the refractory-period signal includes applying the refractory-period signal through the electrode.

In an embodiment, the method includes detecting arrhythmia of the heart, and applying an anti-arrhythmic signal to the cardiac site in response thereto.

In an embodiment, detecting the arrhythmia includes detecting fibrillation of the heart, and applying the anti-arrhythmic signal includes applying a defibrillating signal to the cardiac site in response to the detecting of the fibrillation.

In an embodiment, accessing the cardiac site includes implanting an electrode from a right ventricle of the subject into an interventricular septum of the subject.

In an embodiment, implanting includes implanting a distal tip of the electrode to a depth of 5-10 mm in the septum.

In an embodiment, implanting includes implanting a distal tip of the electrode to a depth of 10-20 mm in the septum.

In an embodiment, implanting includes implanting a distal tip of the electrode to a depth of 20-25 mm in the septum.

In an embodiment, implanting includes implanting the electrode such that a distal tip of the electrode passes through the septum and protrudes into the left ventricle.

In an embodiment, the electrode includes a coil electrode, and implanting the electrode includes implanting the coil electrode.

In an embodiment, implanting the electrode includes screwing the electrode into the septum.

In an embodiment, the electrode includes a bipolar electrode, and screwing the electrode includes screwing the bipolar electrode into the septum.

In an embodiment, applying the refractory-period signal includes applying a series of pulses which are greater than 8 mA.

In an embodiment, applying the refractory-period signal includes applying a series of pulses which are greater than 10 mA.

In an embodiment, applying the refractory-period signal includes configuring the signal to be capable of modifying contractility of the left ventricle of the heart.

In an embodiment, configuring the refractory-period signal includes configuring the signal to be capable of modifying contractility of an interventricular septum of the heart.

In an embodiment, configuring the refractory-period signal includes configuring the signal to be capable of modifying contractility of a right ventricle of the heart.

In an embodiment, configuring the refractory-period signal includes configuring the signal to be capable of increasing contractility of the left ventricle of the heart.

In an embodiment, configuring the refractory-period signal includes configuring the signal to be capable of decreasing contractility of a portion of the heart.

In an embodiment, configuring the refractory-period signal to be capable of decreasing the contractility includes configuring the signal to be capable of decreasing contractility of an interventricular septum of the heart.

There is yet additionally provided, in accordance with an embodiment of the invention, apparatus for applying a signal to a heart of a human subject, including:

a set of one or more electrodes, configured to be passed through a vena cava of the subject and coupled to a cardiac site; and a control unit, configured to alleviate heart failure of the subject by driving the electrode set to apply to the cardiac site, during a refractory period of the site, a refractory-period signal that affects a left ventricle of the heart.

In an embodiment, the control unit is configured to configure the refractory-period signal to increase cardiac output of the heart.

In an embodiment, the control unit is configured to drive the electrode set to apply a series of biphasic pulses.

In an embodiment, the control unit is configured to drive the electrode set to apply a series of generally square pulses.

In an embodiment, the control unit is configured to drive the electrode set to apply a series of pulses at a rate greater than 50 Hz.

In an embodiment, the control unit is configured to drive the electrode set to apply a series of pulses at a rate less than 100 Hz.

In an embodiment, the control unit is configured to drive the electrode set to apply a series of pulses at a rate between 50 Hz and 100 Hz.

In an embodiment, the control unit is configured to drive the electrode set to apply the signal to a site at or adjacent to an intersection of an interventricular septum and a right ventricular free wall.

In an embodiment, at least one of the electrodes includes a material selected from the group consisting of: titanium coated with iridium oxide, titanium coated with titanium nitride, platinum iridium coated with iridium oxide, platinum iridium coated with titanium nitride, platinum iridium coated with sintered platinum, titanium, platinum iridium, and pyrolytic carbon.

In an embodiment, at least one of the electrodes is shaped to define an effective external surface area of between 30 mm2 and 250 mm2.

In an embodiment, at least one of the electrodes has an impedance that is between 50 ohm and 1000 ohm.

In an embodiment, at least one of the electrodes has an impedance that is between 200 ohm and 700 ohm.

In an embodiment, at least one of the electrodes has a capacitance between 300 and 300 microfarads.

In an embodiment, the refractory-period signal includes an excitatory-tissue control (ETC) signal, and the control unit is configured to drive the electrode set to apply signal to the cardiac site.

In an embodiment, the one or more electrodes include a plurality of electrodes, configured to be implanted at a respective plurality of cardiac sites.

In an embodiment, the electrode set includes a bipolar electrode.

In an embodiment, the electrode set includes a monopolar electrode.

In an embodiment, the control unit configures the refractory-period signal to include a series of biphasic pulses.

In an embodiment, the control unit is configured to configure the signal to be capable of modifying contractility of a portion of the heart.

In an embodiment, the control unit is configured to configure the signal to be capable of increasing contractility of the left ventricle of the heart.

In an embodiment, the control unit is configured to configure the signal to be capable of modifying contractility of an interventricular septum of the heart.

In an embodiment, the control unit is configured to configure the signal to be capable of modifying contractility of a right ventricle of the heart.

In an embodiment, the control unit is configured to configure the signal to be capable of increasing contractility of the portion of the heart.

In an embodiment, the control unit is configured to configure the signal to be capable of decreasing contractility of the portion of the heart.

In an embodiment, the control unit is configured to configure the signal to be capable of decreasing contractility of an interventricular septum of the heart.

In an embodiment, the control unit configures the refractory-period signal to include a series of pulses which are greater than 8 mA.

In an embodiment, the control unit configures the refractory-period signal to include a series of pulses which are greater than 10 mA.

In an embodiment, the control unit is configured to drive the electrode set to apply the refractory-period signal chronically.

In an embodiment, the control unit is configured to configure the refractory-period signal to engender long-term alleviation of the heart failure.

In an embodiment, the control unit is configured to drive the electrode set to apply a pacing signal to the site during an excitatory period of a cardiac cycle, and to apply the refractory-period signal during a refractory period of the same cardiac cycle.

In an embodiment, the control unit is configured to drive the electrode set to apply the refractory-period signal with no delay following application of the pacing signal.

In an embodiment, the control unit is configured to drive the electrode set to apply the refractory-period signal following a delay after application of the pacing signal.

In an embodiment, the control unit configures the refractory-period signal to include a plurality of pulses that are greater than 1 mJ.

In an embodiment, the control unit configures the refractory-period signal to include a plurality of pulses that are greater than 5 mJ.

In an embodiment, the control unit is configured to receive a sensed signal indicative of electrical activity of the heart at a sensing site, and to drive the electrode set to apply the refractory-period signal in response to the sensed signal.

In an embodiment, the apparatus includes a sensing electrode which is not an electrode from the electrode set, and the control unit is configured to receive the sensed signal from the sensing electrode.

In an embodiment, the control unit is configured to receive the sensed signal from one of the one or more electrodes in the electrode set, and to drive the one of the one or more electrodes to apply the refractory-period signal in response to the sensed signal.

In an embodiment, the control unit is configured to detect arrhythmia of the heart, and to drive at least one of the electrodes in the electrode set to apply an anti-arrhythmic signal in response thereto.

In an embodiment, the control unit is configured to detect fibrillation of the heart, and to drive the at least one of the electrodes to apply a defibrillating signal to the cardiac site in response to detecting fibrillation.

In an embodiment, the electrode set is configured to be implanted from a right ventricle of the subject into an interventricular septum of the subject.

In an embodiment, at least one of the electrodes is configured to penetrate to a depth of 5-10 mm in the septum.

In an embodiment, at least one of the electrodes is configured to penetrate to a depth of 10-20 mm in the septum.

In an embodiment, at least one of the electrodes is configured to penetrate to a depth of 20-25 mm in the septum.

In an embodiment, at least one of the electrodes is configured to penetrate through the septum and emerge in the left ventricle.

In an embodiment, at least one of the electrodes includes a coil electrode.

In an embodiment, at least one of the electrodes includes a screw electrode, configured to be screwed into the septum.

In an embodiment, the screw electrode includes a bipolar screw electrode.

The present invention will be more fully understood from the following detailed description of the preferred embodiments thereof, taken together with the drawings, in which:

DETAILED DESCRIPTION OF PREFERRED EMBODIMENTS

Figure 1A:
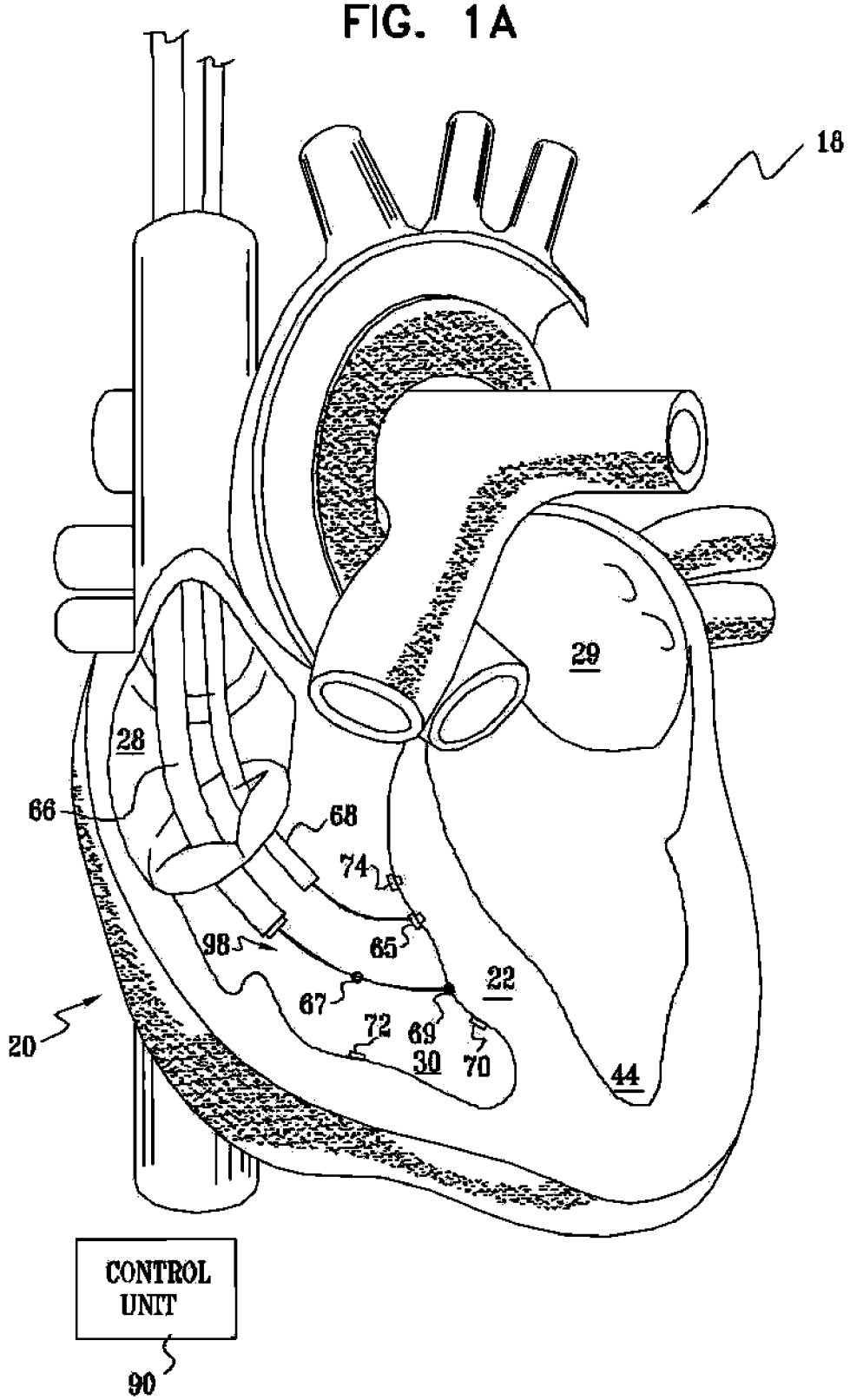
FIGS. 1A, 1B, and 1C are schematic, sectional illustrations of a heart, showing the placement of electrodes therein, in accordance with preferred embodiments of the present invention.

FIG. 1A is a schematic illustration of cardiac control apparatus 18, which applies electrical energy to improve the performance of the heart 20 of a patient, in accordance with a preferred embodiment of the present invention. Apparatus 18 preferably comprises an implantable or external control unit 90, which applies an ETC signal through a set of one or more electrodes 98 to the heart. (For clarity, connections between control unit 90 and the various electrodes are not shown).

Preferably, a catheter 68 is used to convey a screw electrode 65, or other type of electrode, through the right ventricle 30 to a site on the interventricular septum 22 to which the electrode is attached. Alternatively or additionally, a catheter 66 conveys an electrode 69 through the right ventricle to be fixed to the septum, and/or conveys an electrode 67 into the right ventricle, where it is in electrical contact with electrodes 65 and 69 through the blood in the right ventricle. In a preferred embodiment one or more electrodes are placed at or adjacent to the intersection of the septum and the right ventricular free wall.

Preferably, at least some of the electrodes have a coating applied thereto which increases the electrodes' capacitance. A preferred coating comprises iridium oxide (IROX). Alternatively or additionally, at least some of the electrodes comprise coils, a mesh, or other means for increasing the effective application area of the ETC signal.

As described hereinbelow, control unit 90 drives one or more of the electrodes to apply an ETC signal to the septum, so as to modify an aspect of the heart's contractility. For example, the signal may be applied so as to increase or decrease contractility of the right ventricle, the left ventricle, or the septum. Optionally, the control unit is implanted in the patient's body, and a metal case of the control unit serves as a return electrode for current driven through the electrodes in right ventricle 30.

Preferably, aspects of ETC signal application are performed in accordance with techniques described in the above-referenced U.S. patent application Ser. Nos. 09/101,723 and 09/254,900. Typically, the ETC signal is applied subsequent to an artificial pacing pulse, as described hereinbelow. Alternatively, the ETC signal is applied responsive to natural electrical activity of the heart, for example, after a designated delay following a detected activation of the atrium. For these applications, it is preferable to use apparatus and methods described in Israel Patent Application 129,257, entitled "Trigger-based regulation of excitable tissue control in the heart," which is assigned to the assignee of the present invention and is incorporated herein by reference.

Control unit 90 is optionally coupled to one or more local sense electrodes 74, which are placed in the right ventricle or elsewhere on or in the heart. Local sense electrodes 74 preferably convey electrical signals to the control unit responsive to cardiac electric activity. Alternatively or additionally, one or more of electrodes 98 and any other electrodes coupled to control unit 90 may also serve as sense electrodes. Optionally, one or more mechanical sensors 70 (e.g., accelerometers, force transducers, strain gauges, or pressure gauges), coupled to the control unit, are placed on the right ventricle or elsewhere on the heart. Alternatively or additionally, one or more supplemental sensors 72 (e.g., blood pressure, thoracic electrical impedance, pH, SvO2, pCO2 or pO2 sensors) are coupled to the control unit and are placed on or in the heart or elsewhere on or in the patient's body. The control unit modifies the energy applied through electrodes 98 responsive to signals from sensors 70 and 72 and local sense electrodes 74, as described hereinbelow.

The number of electrodes and sensors, as well as the positions thereof, are shown in FIG. 1A by way of example, and other sites on heart 20 or in a vicinity thereof are appropriate for placement of some of the electrodes and sensors in other applications of the present invention.

Preferably, control unit 90 is implanted in the patient in a manner similar to that used to implant pacemakers or defibrillators known in the art, such that after an initial calibration period, described hereinbelow, the unit is generally able to automatically modify the ETC signal it applies to the heart as needed, so as to maintain a desired level of performance. In many applications, standard pacing, cardioversion, and defibrillation capabilities are additionally incorporated into apparatus 18.

Figure 1B:
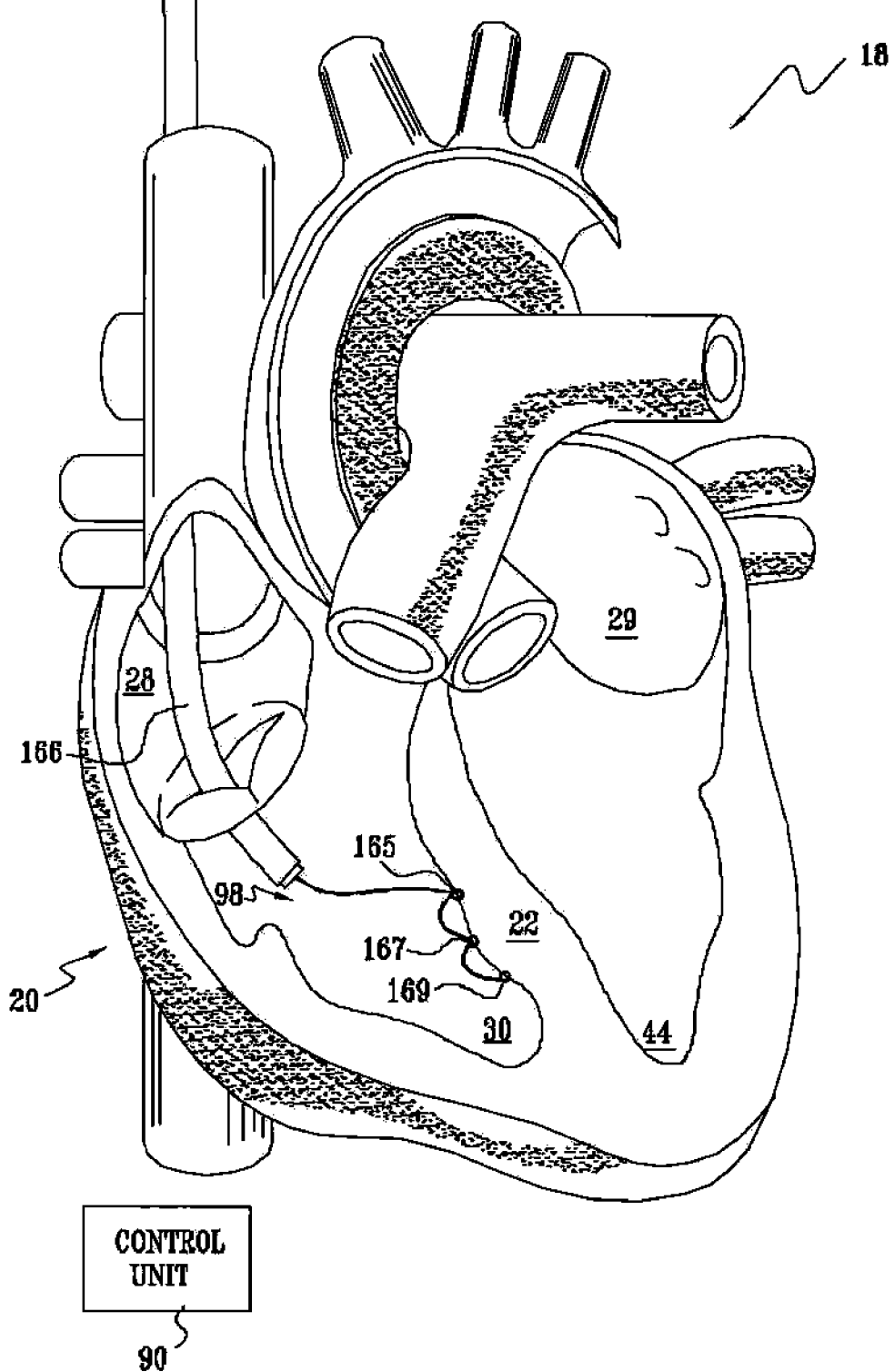
Figure 1C:
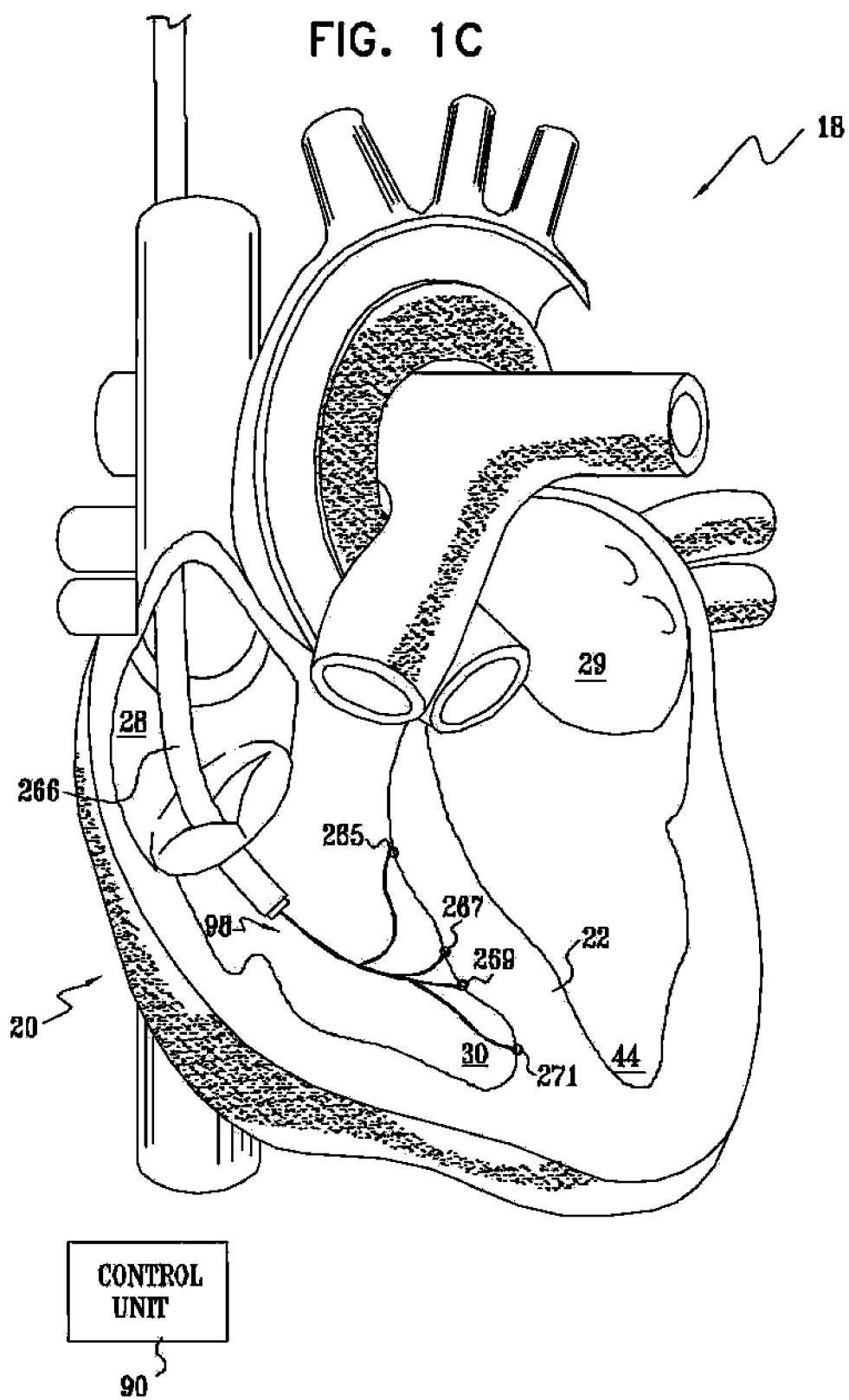

FIGS. 1B and 1C are schematic illustrations of other preferred configurations of cardiac control apparatus 18, in accordance with respective preferred embodiments of the present invention. FIG. 1B shows a catheter 166, which conveys a plurality of electrodes 165, 167, and 169 to respective sites on the right ventricular septum, while FIG. 1C shows a catheter 266, which conveys a different arrangement of electrodes 265, 267, 269, and 271 to the septum. In another preferred embodiment (not shown), a catheter passes a basket electrode into the right ventricle, so as to apply the ETC signal to the septum as well as to other right ventricular sites. Preferably, but not necessarily, all of the electrodes shown in FIGS. 1A, 1B, and 1C are independently controlled by control unit 90.

Figure 2:
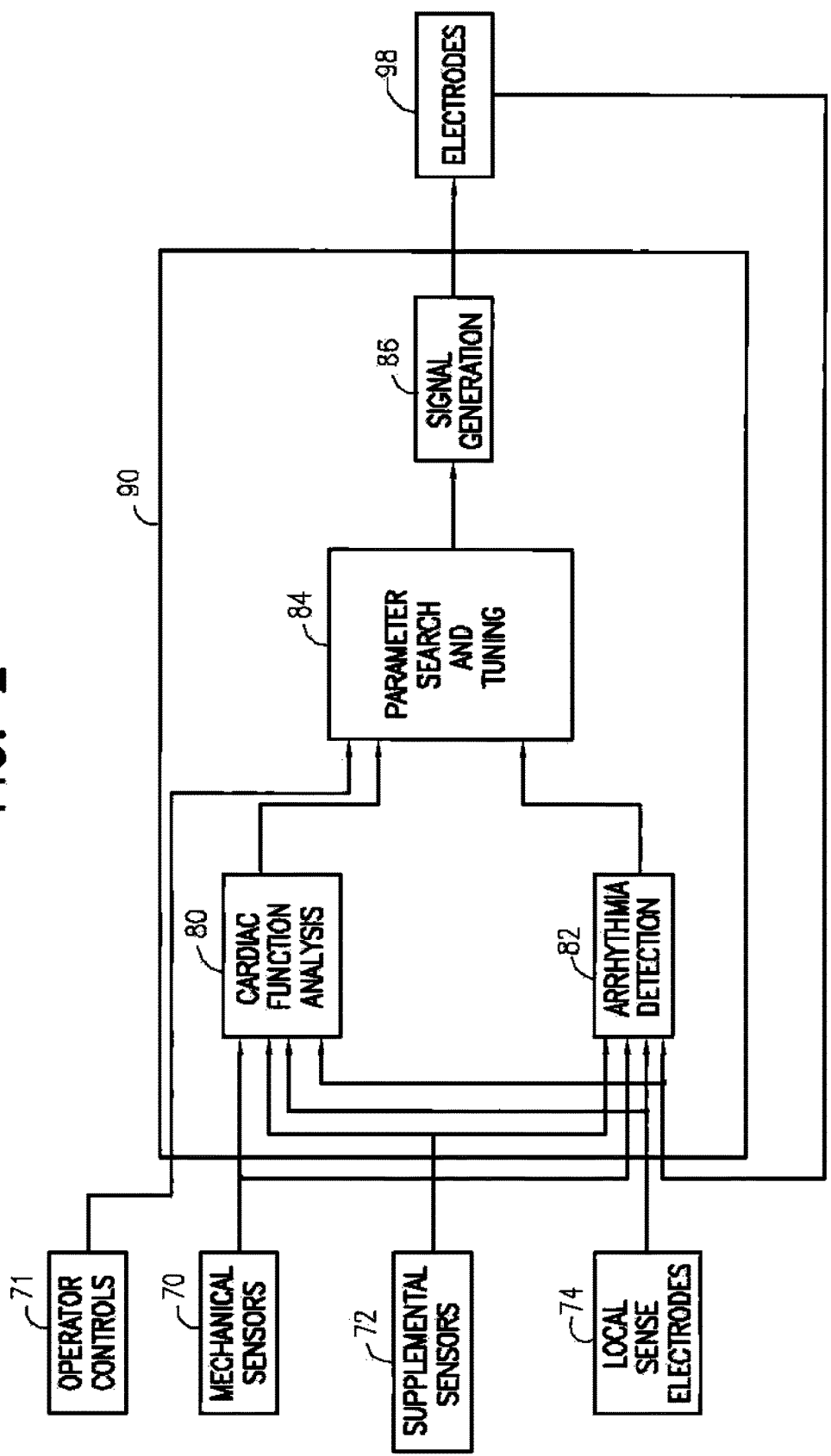
FIG. 2 is a schematic block diagram of a control unit, which generates signals to be applied to the electrodes shown in FIGS. 1A, 1B, and/or 1C, in accordance with a preferred embodiment of the present invention.

FIG. 2 is a schematic block diagram of control unit 90, in accordance with a preferred embodiment of the present invention. Mechanical sensors 70, supplemental sensors 72, local sense electrodes 74, and electrodes 98 are preferably coupled to provide feedback signals to a cardiac function analysis block 80 of control unit 90. The feedback signals generally provide information about various aspects of the heart's performance to block 80, which analyzes the signals and actuates control unit 90 to modify the electrical energy applied to the heart responsive to the analysis. Preferably, the ETC signal is adjusted by the control unit responsive to the feedback signals in order to yield a desired response, e.g., a predetermined blood pressure, blood oxygen level, cardiac output and/or cardiac electrical or motion profile.

Preferably, block 80 conveys results of its analysis to a "parameter search and tuning" block 84 of control unit 90, which iteratively modifies characteristics of the electrical energy applied to the heart in order to attain a desired response. Preferably, operating parameters of block 84 are entered by a human operator of the control unit using operator controls 71, which typically comprise a keyboard or mouse (not shown) coupled to the control unit. Block 84 typically utilizes multivariate optimization and control methods known in the art in order to cause one or more of the aforementioned mechanical, electrical, chemical and/or other measured parameters to converge to desired values.

In general, each one of electrodes 98 may convey a particular waveform to heart 20, differing in certain aspects from the waveforms applied by the other electrodes. The particular waveform to be applied by each electrode is determined by control unit 90, preferably under the control of the operator. Aspects of the waveforms which are set by the control unit, and may differ from electrode to electrode, typically include parameters such as time shifts between application of waveforms at different electrodes, waveform shapes, amplitudes, DC offsets, durations, and duty cycles. For example, although the waveforms applied to some or all of electrodes 98 usually comprise a biphasic square wave signal following a natural or applied pacing pulse, other waveforms, such as a sinusoid, a series of monophasic square waves, or a waveform including an exponentially-varying characteristic, could be applied to other electrodes. Generally, the shape, magnitude, and timing of the waveforms are optimized for each patient, using suitable optimization algorithms as are known in the art.

For the purposes of this embodiment of the present invention, block 84 typically modifies a set of controllable parameters of the ETC signal, responsive to the measured parameters, in accordance with values in a look-up table and/or pre-programmed formulae stored in an electronic memory of control unit 90. The controllable parameter may comprise, for example, ETC signal timing, magnitude and offset. Preferably, the controllable parameters are conveyed by block 84 to a signal generation block 86 of control unit 90, which generates, responsive to the parameters, electrical signals that are applied by electrodes 98 to the heart. Block 86 preferably comprises amplifiers, isolation units, and other standard circuitry known in the art of electrical signal generation.

In the initial calibration procedure, parameter search and tuning block 84 preferably modifies a characteristic (e.g., timing, magnitude, or shape) of the ETC signal applied through one of electrodes 98, and then determines whether a predetermined cardiac functional response generally improves following the modification. For example, the electrode may be used to sense the duration of the refractory period of heart tissue to which the electrode is coupled, and block 84 may subsequently determine time points during the refractory period which are optimal for application of the ETC signal by that electrode to the tissue. In a series of similar calibration steps, block 84 repeatedly modifies characteristics of the energy applied through each of the electrodes, such that those modifications that improve the response are generally maintained, and modifications that cause it to worsen are typically eliminated or avoided.

When apparatus 18 is calibrated in the presence of a physician, it is often desirable to have the patient perform increasing levels of exercise (e.g., walk on a treadmill), in order to derive a broader range of operating parameters, which are stored in control unit 90 and can be accessed responsive to signals from the sensors and electrodes coupled to the control unit. Preferably, the calibration procedure is subsequently performed by the physician at intermittent follow-up visits, and/or by unit 90 automatically during regular use of the apparatus (e.g., daily).

Preferably, during the initial calibration procedure, the locations of one or more of electrodes 98 are varied while the ETC signal is applied therethrough, so as to determine optimum placement of the electrodes. Preferably, methods for measuring the heart's response to the applied signal include electrocardiography, echocardiography, and/or methods having as inputs the outputs of mechanical and supplemental sensors 70 and 72. In subsequent steps, the electrode is moved over an area of the interventricular septum, and the response of the heart is measured. After the physician considers that a sufficient number of sites have been investigated, the electrode is returned to the site yielding the best response. Subsequently, other electrodes are moved according to the same protocol, so as to achieve substantially optimum placement of some or all of the electrodes.

In a preferred embodiment, the ETC signal is applied in a vicinity of a site where standard pacing pulses are applied. Preferably, the ETC signal is applied through the same electrode as that through which the standard pacing pulse is applied, approximately 1-250 ms thereafter. Further preferably, the ETC signal is applied approximately 20-250 ms after the pacing pulse.

Alternatively, the sinoatrial node generates the cardiac rhythm, substantially without artificial pacing. In such modes, local sense electrodes 74 and, optionally, some or all of electrodes 98, convey electrical signals to control unit 90, so as to enable parameter search and tuning block 84 to synchronize the electrical signals applied by electrodes 98 with the natural electrical activity of the heart. It will be understood that although electrodes 74 and 98 are shown for clarity of explanation as separate entities, a single set of electrodes may be used to perform both functions.

In a preferred embodiment, the ETC signal is applied at one or more sites as a series of pulses, e.g., biphasic square pulses, typically having a frequency between about 50 and 100 Hz. The current applied during each pulse is preferably greater than 8 mA, and, further preferably, greater than 10 mA.

Most preferably, during calibration and during regular operation of control unit 90, an arrhythmia detection block 82 of control unit 90 receives inputs from sensors 70 and 72 and electrodes 74 and 98, and/or other electrodes and sensors (not shown), and evaluates these inputs to detect imminent or actual cardiac arrhythmia, e.g., an ectopic heartbeat, fibrillation, bradycardia or heart block. Preferably, block 82 employs techniques known in the art for detecting arrhythmias, so that parameter search and tuning block 84 can treat or terminate the arrhythmia by applying, for example, regular pacing pulses or defibrillation pulses.

Figure 3:
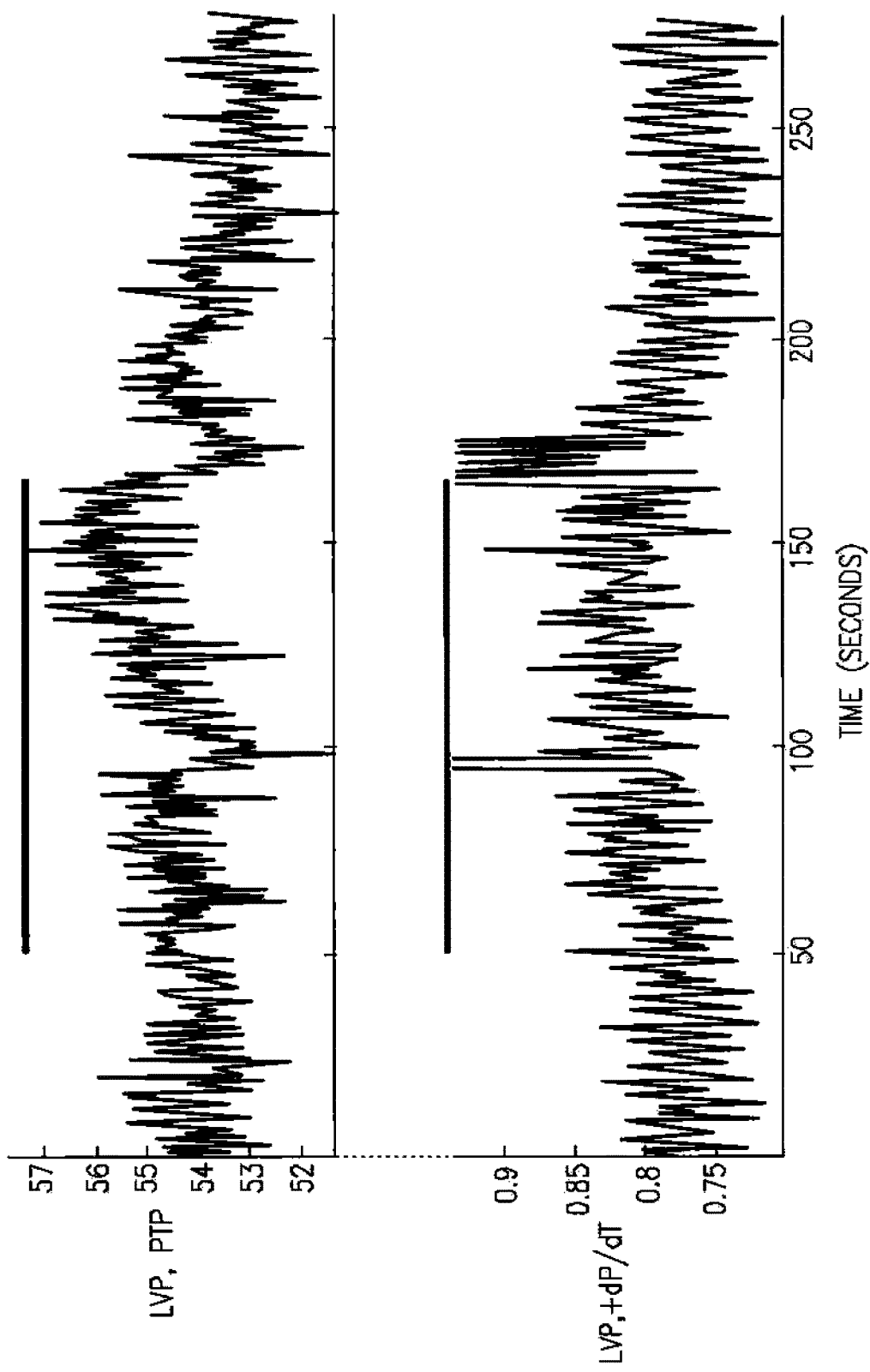
FIGS. 3, 4, and 5 are graphs showing experimental results from the application of an ETC signal to an animal heart, in accordance with a preferred embodiment of the present invention.
Figure 4:
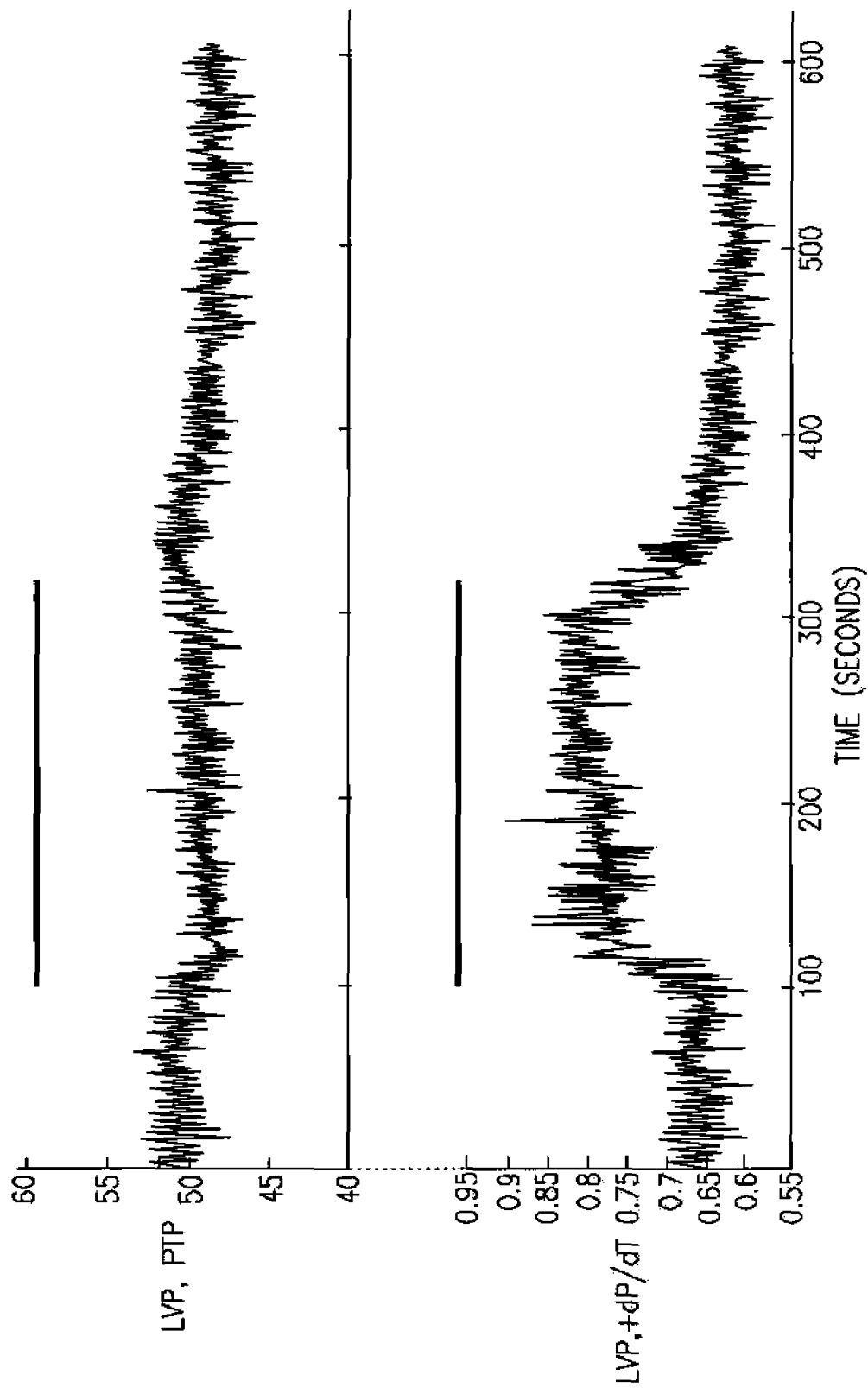
Figure 5:
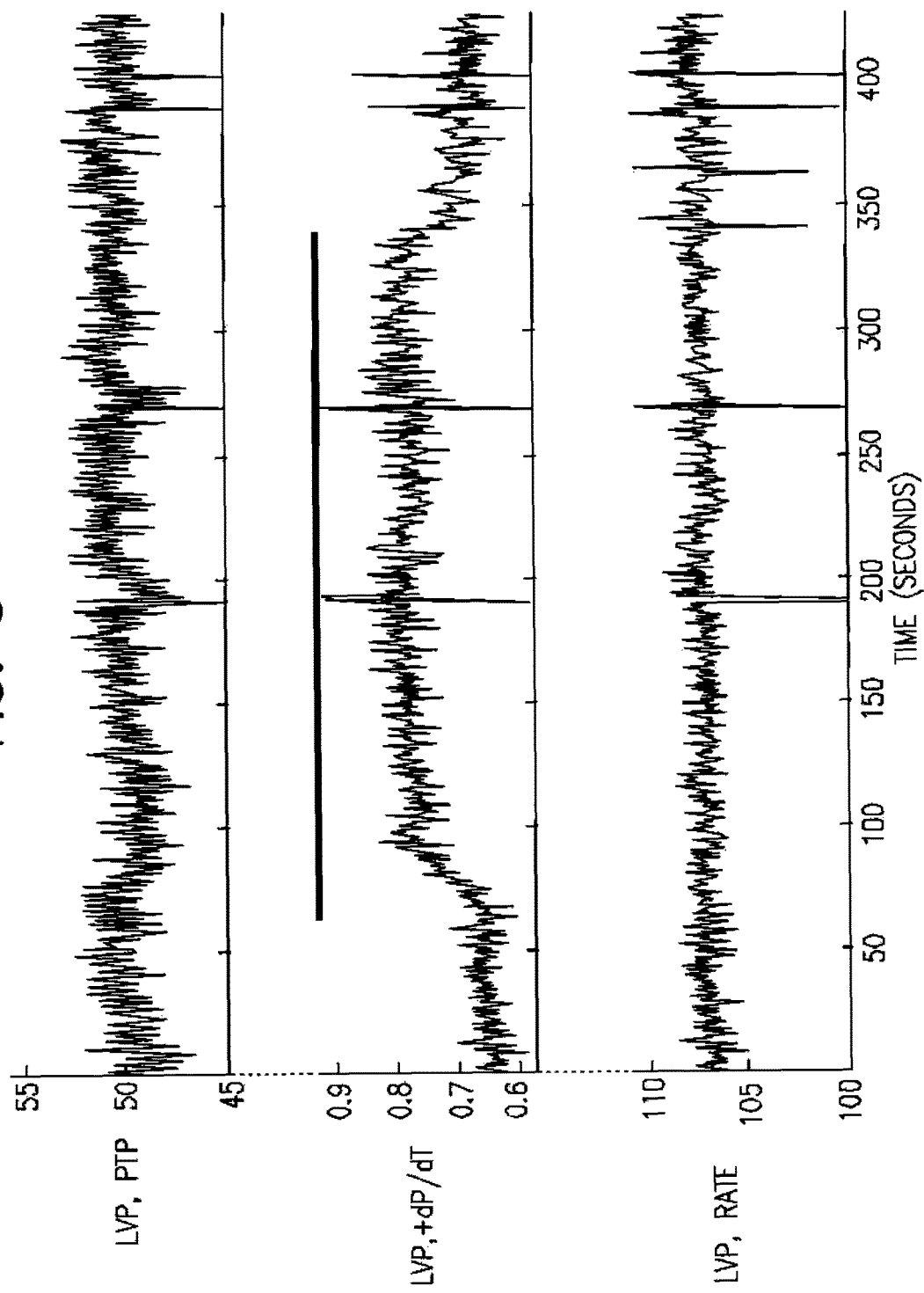

FIGS. 3, 4, and 5 are graphs showing experimental results obtained during application of an ETC signal to a 30 kg anesthetized pig, in accordance with a preferred embodiment of the present invention. In this experiment, local sense electrodes comprised two stitch electrodes, which were placed at the mid-anterior wall of the left ventricle. The animal was paced in DDD mode at 120 beats per minute through an active fixation screw electrode, placed in the apical third of the right ventricular septum. At 20 ms following the onset of electrical activity as measured by the local sense electrodes, a biphasic electrical signal, composed of a 15 ms, +14 mA pulse immediately followed by a 15 ms, −14 mA pulse, was applied to the septum through the screw electrode implanted therein. In FIG. 3, results are shown following application of the ETC signal between the screw electrode implanted in the septum and a ring electrode in a vicinity thereof. FIGS. 4 and 5 show results following application of the ETC signal between the screw electrode and a stitch electrode at the mid-anterior left ventricular free wall.

In FIG. 3, an increase of approximately 5% in the measured d(LVP)/dt is seen to begin upon initiation of a 2 minute ETC signal application period. The dP/dt levels gradually return to baseline upon termination of the ETC signal. FIGS. 4 and 5 show bipolar ETC application periods lasting over 3 and over 4 minutes, respectively, in which the measured dP/dt increased to approximately 20% above baseline, and remained at this level for the duration of signal application.

It is believed that at least some of the results displayed in FIGS. 3, 4, and 5 derive from a change in contractility of the left ventricle induced by the application of the ETC signal to the interventricular septum.

It is also believed that similar results can be obtained in humans, mutatis mutandis. It is further believed that these embodiments of the present invention can produce, at least to some extent, long-term effects which are likely to alleviate or cure aspects of some common cardiac pathologies, such as congestive heart failure (CHF). These effects are expected to derive from more effective use of the heart muscle, whereby systemic demands on the heart are reduced. Moreover, damage to other organs of the body is reduced, because of the increase in blood perfusion.

It is believed that other signal application protocols would also be successful in enhancing cardiac performance, in combination with or in the absence of some of the stimulation and sensing protocols described hereinabove. In a preferred embodiment the ETC signal is applied at a plurality of sites on the interventricular septum, for example, on an anterior and a posterior aspect thereof. Alternatively or additionally, the ETC signal is applied generally simultaneously, or in alternation, at one or more of the following sites: the posterior septum, the anterior septum, the anterior wall of the right ventricle, the free wall of the right ventricle, and the posterior-inferior left ventricular free wall.

Alternatively or additionally, the ETC signal is applied through the right ventricular septum so as to decrease regional contractility of the heart, preferably using techniques described in one or both of the above-referenced US patent applications. In particular, the ETC signal may be used to decrease septal contractility, which may be appropriate in treating conditions such as idiopathic hypertrophic subaortic stenosis (IHSS). It is believed that reduced septal contractility reduces functional subaortic stenosis, thereby improving left ventricular performance.

In an embodiment, embodiments of the present invention are practiced using methods and apparatus described in US Patent Application Publication 2002/0055764 to Malonek et al., which is incorporated herein by reference.

It will be appreciated by persons skilled in the art that the present invention is not limited to what has been particularly shown and described hereinabove. Rather, the the present invention includes both combinations and sub-combinations of the various features described hereinabove, as well as variations and modifications thereof that are not in the prior art which would occur to persons skilled in the art upon reading the foregoing description.

The invention claimed is:

1. Apparatus for applying a signal to a heart of a human subject, comprising: one or more electrodes, configured to be passed by a catheter through a vena cava of the subject and coupled to a cardiac site of the right ventricle or the right ventricle septum of the subject; a circuitry for determining a start time of or a time within a refractory period; and a control unit, configured to alleviate heart failure of the subject by driving the one or more electrodes to apply to said cardiac site, during said determined refractory period of the site, a signal that directly affects a left ventricle of the heart and is non-excitatory thereto.

2. The apparatus according to claim 1, wherein the one or more electrodes are configured to be implanted from a right ventricle of the subject into an inter-ventricular septum of the subject.

3. The apparatus according to claim 2, wherein at least one of the electrodes is configured to penetrate to a depth of 5-10 mm in the septum.

4. The apparatus according to claim 2, wherein at least one of the electrodes is configured to penetrate to a depth of 10-20 mm in the septum.

5. The apparatus according to claim 2, wherein at least one of the electrodes is configured to penetrate to a depth of 20-25 mm in the septum.

6. The apparatus according to claim 2, wherein at least one of the electrodes is configured to penetrate through the septum and emerge in the left ventricle.

7. The apparatus according to claim 2, wherein at least one of the electrodes comprises a coil electrode.

8. The apparatus according to claim 2, wherein at least one of the electrodes comprises a screw electrode, configured to be screwed into the septum.

9. The apparatus according to claim 8, wherein the screw electrode comprises a bipolar screw electrode.

10. The apparatus according to claim 1, wherein the control unit is operative to configure the signal to be capable of modifying contractility of a portion of the heart.

11. The apparatus according to claim 10, wherein the control unit is operative to configure the signal to be capable of increasing contractility of the left ventricle of the heart.

12. The apparatus according to claim 10, wherein the control unit is operative to configure the signal to be capable of modifying contractility of an inter-ventricular septum of the heart.

13. The apparatus according to claim 10, wherein the control unit is operative to configure the signal to be capable of modifying contractility of a right ventricle of the heart.

14. The apparatus according to claim 10, wherein the control unit is operative to configure the signal to be capable of increasing contractility of the portion of the heart.

15. The apparatus according to claim 10, wherein the control unit is operative to configure the signal to be capable of decreasing contractility of the portion of the heart.

16. The apparatus according to claim 15, wherein the control unit is operative to configure the signal to be capable of decreasing contractility of an inter-ventricular septum of the heart.

17. The apparatus according to claim 1, wherein the control unit is configured to drive the one or more electrodes to apply a pacing signal to the site during an excitatory period of a cardiac cycle, and to apply the refractory-period signal during a refractory period of the same cardiac cycle.

18. The apparatus according to claim 17, wherein the control unit is configured to drive the one or more electrodes to apply the refractory-period signal with no delay following application of the pacing signal.

19. The apparatus according to claim 17, wherein the control unit is configured to drive the one or more electrodes to apply the refractory-period signal following a delay after application of the pacing signal.

20. The apparatus according to claim 1, wherein the control unit is configured to receive a sensed signal indicative of electrical activity of the heart at a sensing site, and to drive the one or more electrodes to apply the refractory-period signal in response to the sensed signal.

21. The apparatus according to claim 20, comprising a sensing electrode which is separate from the one or more electrodes, wherein the control unit is configured to receive the sensed signal from the sensing electrode.

22. The apparatus according to claim 20, wherein the control unit is configured to receive the sensed signal from one of the one or more electrodes, and to drive the one of the one or more electrodes to apply the refractory-period signal in response to the sensed signal.

23. The apparatus according to claim 1, wherein the control unit configures the refractory-period signal to include a series of pulses which are greater than 8 mA.

24. The apparatus according to claim 23, wherein the control unit configures the refractory-period signal to include a series of pulses which are greater than 10 mA.

25. The apparatus according to claim 1, wherein the control unit is configured to drive the one or more electrodes to apply the refractory-period signal chronically.

26. The apparatus according to claim 25, wherein the control unit is operative to configure the refractory-period signal to engender long-term alleviation of the heart failure.

27. The apparatus according to claim 1, wherein the control unit configures the refractory-period signal to include a plurality of pulses that are greater than 1 mJ.

28. The apparatus according to claim 27, wherein the control unit configures the refractory-period signal to include a plurality of pulses that are greater than 5 mJ.

29. The apparatus according to claim 1, wherein the control unit is configured to detect arrhythmia of the heart, and to drive at least one of the one or more electrodes to apply an anti-arrhythmic signal in response thereto.

30. The apparatus according to claim 29, wherein the control unit is configured to detect fibrillation of the heart, and to drive the at least one of the electrodes to apply a defibrillating signal to the cardiac site in response to detecting fibrillation.

31. The apparatus according to claim 1, wherein said cardiac site is a cardiac site of the right ventricle septum of the subject.

32. The apparatus according to claim 31, wherein the signal applied to the right ventricle septum of the subject increases contractility efficacy of the left ventricle.

33. The apparatus according to claim 1, wherein the control unit is operative to configure the refractory-period signal such that it increases cardiac output of the heart.

34. The apparatus according to claim 1, wherein the control unit is configured to drive the one or more electrodes to apply a series of biphasic pulses.

35. The apparatus according to claim 1, wherein the control unit is configured to drive the one or more electrodes to apply a series of generally square pulses.

36. The apparatus according to claim 1, wherein the control unit is configured to drive the one or more electrodes to apply a series of pulses at a rate greater than 50 Hz.

37. The apparatus according to claim 1, wherein the control unit is configured to drive the one or more electrodes to apply a series of pulses at a rate less than 100 Hz.

38. The apparatus according to claim 1, wherein the control unit is configured to drive the one or more electrodes to apply a series of pulses at a rate between 50 Hz and 100 Hz.

39. The apparatus according to claim 1, wherein the control unit is configured to drive the one or more electrodes to apply the signal to a site at or adjacent to an intersection of an interventricular septum and a right ventricular free wall.

40. The apparatus according to claim 1, wherein at least one of the electrodes comprises a material selected from the group consisting of: titanium coated with iridium oxide, titanium coated with titanium nitride, platinum iridium coated with iridium oxide, platinum iridium coated with titanium nitride, platinum iridium coated with sintered platinum, titanium, platinum iridium, and pyrolytic carbon.

41. The apparatus according to claim 1, wherein at least one of the electrodes is shaped to define an effective external surface area of between 30 $mm^2$ and 250 $mm^2$.

42. The apparatus according to claim 1, wherein at least one of the electrodes has an impedance that is between 50 Ohms and 1000 Ohms.

43. The apparatus according to claim 1, wherein at least one of the electrodes has an impedance that is between 200 Ohms and 700 Ohms.

44. The apparatus according to claim 1, wherein at least one of the electrodes has a capacitance between 300 and 3000 microfarads.

45. The apparatus according to claim 1, wherein the refractory-period signal includes an excitatory-tissue control (ETC) signal, and wherein the control unit is configured to drive the one or more electrodes to apply the ETC signal to the cardiac site.

46. The apparatus according to claim 1, wherein the one or more electrodes comprise a plurality of electrodes, configured to be implanted at a respective plurality of cardiac sites.

47. The apparatus according to claim 1, wherein the one or more electrodes comprise a bipolar electrode.

48. The apparatus according to claim 1, wherein the one or more electrodes comprise a monopolar electrode.

49. The apparatus according to claim 1, wherein the control unit configures the refractory-period signal to include a series of biphasic pulses.

50. The apparatus according to claim 1, including a plurality of electrodes, and wherein the control system is operable to apply different signals to one or more of the electrodes.

* * * * *